(12) United States Patent
Nothacker et al.

(10) Patent No.: US 10,034,635 B2
(45) Date of Patent: *Jul. 31, 2018

(54) METHOD AND SYSTEM FOR MONITORING INTOXICATION

(71) Applicant: KHN Solutions, Inc., San Francisco, CA (US)

(72) Inventors: Keith Harry Nothacker, San Francisco, CA (US); Pauline Anne Basaran, San Francisco, CA (US); Stacey Ilene Rettus, San Francisco, CA (US); Micahel Jurgen Strasser, San Francisco, CA (US); Imraan Aziz, San Francisco, CA (US); John Paul Walton, San Francisco, CA (US); Zachary Michael Saul, San Francisco, CA (US); Christopher Thomas Faykus, San Francisco, CA (US)

(73) Assignee: KHN Solutions, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/459,820

(22) Filed: Mar. 15, 2017

(65) Prior Publication Data

US 2017/0181696 A1    Jun. 29, 2017

Related U.S. Application Data

(63) Continuation of application No. 15/294,317, filed on Oct. 14, 2016, which is a continuation of application
(Continued)

(51) Int. Cl.
*G08B 23/00* (2006.01)
*A61B 5/00* (2006.01)
(Continued)

(52) U.S. Cl.
CPC .......... *A61B 5/4845* (2013.01); *A61B 5/0022* (2013.01); *A61B 5/082* (2013.01);
(Continued)

(58) Field of Classification Search
CPC ................ G08B 21/02; G08B 21/0453; G01N 33/4972; A61B 5/18; A61B 5/082;
(Continued)

(56) References Cited

U.S. PATENT DOCUMENTS 4,487,055 A    12/1984 Wolf
4,749,553 A    6/1988 Lopez et al.
(Continued)

FOREIGN PATENT DOCUMENTS

FR    2975522    11/2012

OTHER PUBLICATIONS

FR2975522A1—preview.pdf—English Abstract of FR2975522A1.
STIC Search Results. 15205876-528781—Search Results.pdf.

*Primary Examiner* — Thomas Mullen
(74) *Attorney, Agent, or Firm* — Jeffrey Schox; Diana Lin

(57) ABSTRACT

A method and system for monitoring a user's intoxication including receiving a set of signals, derived from a set of samples collected from the user at a set of time points; providing a sobriety task to the user proximal to a time point of the set of time points; generating a performance dataset characterizing performance of the sobriety task by the user; receiving a supplementary dataset characterizing a demographic profile of the user and/or a physiological state of the user; determining a set of values of an intoxication metric, derived from the set of signals; generating a predicted temporal profile of the intoxication metric for the user based upon the set of values, the set of time points, and the supplementary dataset; generating an analysis of the user's sobriety based upon the performance dataset and the pre-
(Continued)

dicted temporal profile; and providing a notification to the user based upon the analysis.

21 Claims, 19 Drawing Sheets

Related U.S. Application Data

No. 14/925,675, filed on Oct. 28, 2015, now Pat. No. 9,662,065, which is a continuation of application No. 14/631,125, filed on Feb. 25, 2015, now Pat. No. 9,192,334, which is a continuation-in-part of application No. 14/470,376, filed on Aug. 27, 2014, now Pat. No. 9,076,317, which is a continuation of application No. 14/169,029, filed on Jan. 30, 2014, now Pat. No. 8,878,669.

(60) Provisional application No. 61/759,390, filed on Jan. 31, 2013, provisional application No. 61/812,704, filed on Apr. 16, 2013.

(51) Int. Cl.
*A61B 5/08* (2006.01)
*A61B 5/097* (2006.01)
*A61B 5/11* (2006.01)
*G01N 33/497* (2006.01)
*G08B 21/04* (2006.01)
*A61B 10/00* (2006.01)

(52) U.S. Cl.
CPC ............ *A61B 5/097* (2013.01); *A61B 5/1118* (2013.01); *A61B 5/4023* (2013.01); *A61B 5/486* (2013.01); *A61B 5/681* (2013.01); *A61B 5/7282* (2013.01); *A61B 5/742* (2013.01); *A61B 5/7475* (2013.01); *G01N 33/4972* (2013.01); *G08B 21/0453* (2013.01); *A61B 2010/0009* (2013.01); *A61B 2010/0087* (2013.01); *A61B 2503/22* (2013.01); *A61B 2562/0219* (2013.01)

(58) Field of Classification Search
CPC ..... A61B 5/4845; A61B 5/7275; A61B 5/742; A61B 5/7475; A61B 5/4023; A61B 5/4863; A61B 5/0022; A61B 5/097; A61B 5/486; A61B 5/681; A61B 5/1118; A61B 5/7282
USPC ............ 340/576, 439, 539.12; 600/300, 309
See application file for complete search history.

(56) References Cited

U.S. PATENT DOCUMENTS

| | | |
|---|---|---|
| 4,996,161 A | 2/1991 | Conners et al. |
| D333,441 S | 2/1993 | Greene |
| 5,216,415 A | 6/1993 | Ono et al. |
| 5,291,898 A | 3/1994 | Wolf |
| D362,642 S | 9/1995 | Howse |
| D381,885 S | 8/1997 | Lane |
| 5,944,661 A | 8/1999 | Swette et al. |
| 6,433,863 B1 | 8/2002 | Weiss |
| 6,454,723 B1 | 9/2002 | Montagnino |
| 6,556,905 B1 | 4/2003 | Mittelsteadt et al. |
| 6,608,399 B2 | 8/2003 | McConnell et al. |
| 6,726,636 B2 | 4/2004 | Der Ghazarian et al. |
| 6,824,520 B2 | 11/2004 | Orr et al. |
| 6,899,683 B2 | 5/2005 | Mault et al. |
| 6,956,484 B2 | 10/2005 | Crespo |
| D521,885 S | 5/2006 | Eddy et al. |
| D530,424 S | 10/2006 | Manser et al. |
| D539,683 S | 4/2007 | Shaw et al. |
| D539,684 S | 4/2007 | Kitamura et al. |
| 7,204,335 B2 | 4/2007 | Stewart et al. |
| 7,341,693 B2 | 3/2008 | Der Ghazarian et al. |
| 7,451,852 B2 | 11/2008 | Stewart et al. |
| D586,677 S | 2/2009 | Nothacker et al. |
| D603,281 S | 11/2009 | Gonzalez |
| D606,434 S | 12/2009 | Castrodale et al. |
| 7,823,681 B2 | 11/2010 | Crespo et al. |
| 7,930,927 B2 | 4/2011 | Cooper et al. |
| 8,040,233 B2 | 10/2011 | Adappa et al. |
| 8,126,735 B2 | 2/2012 | Dicks et al. |
| 8,258,968 B2 | 9/2012 | Ghazarian et al. |
| 8,280,436 B2 | 10/2012 | Harris, Jr. |
| 8,370,027 B2 | 2/2013 | Pettersson et al. |
| 8,381,573 B2 | 2/2013 | Keays |
| 8,453,492 B2 | 6/2013 | Tsuzuki et al. |
| 8,693,597 B2 | 4/2014 | Sexton et al. |
| 8,707,758 B2 | 4/2014 | Keays |
| D705,100 S | 5/2014 | Nothacker et al. |
| 8,808,228 B2 | 8/2014 | Brister et al. |
| 8,814,804 B2 | 8/2014 | Walden et al. |
| 8,849,387 B2 | 9/2014 | Gilbert et al. |
| 8,878,669 B2 | 11/2014 | Nothacker et al. |
| 8,920,725 B2 | 12/2014 | Withrow, III et al. |
| 8,941,501 B1 | 1/2015 | Debijl |
| D724,980 S | 3/2015 | Nothacker et al. |
| D727,763 S | 4/2015 | Nothacker et al. |
| D727,764 S | 4/2015 | Nothacker et al. |
| 9,020,773 B2 | 4/2015 | Son et al. |
| D731,341 S | 6/2015 | Kobayakawa |
| 9,045,101 B2 | 6/2015 | Phelan |
| 9,063,120 B2 | 6/2015 | Park |
| 9,076,317 B2 | 7/2015 | Nothacker et al. |
| 9,095,251 B2 | 8/2015 | Purks et al. |
| 9,192,324 B2 | 11/2015 | Phillips et al. |
| 9,192,334 B2 | 11/2015 | Nothacker et al. |
| 9,228,997 B2 | 1/2016 | Keays |
| 9,241,661 B2 | 1/2016 | Shnaper et al. |
| 9,278,696 B2 | 3/2016 | Yi et al. |
| 9,398,858 B2 | 7/2016 | Phillips et al. |
| 9,417,232 B2 | 8/2016 | Keays et al. |
| 9,481,245 B2 | 11/2016 | Nelson |
| 9,600,632 B2 | 3/2017 | Nothacker et al. |
| 9,662,065 B2 * | 5/2017 | Nothacker ............... A61B 5/18 |
| 9,775,565 B1 | 10/2017 | Berg-Neuman et al. |
| 2002/0128769 A1 | 9/2002 | Der Ghazarian et al. |
| 2003/0176803 A1 | 9/2003 | Gollar |
| 2006/0217625 A1 | 9/2006 | Forrester, Jr. |
| 2006/0293613 A1 | 12/2006 | Fatehi et al. |
| 2007/0093725 A1 | 4/2007 | Shaw |
| 2009/0043409 A1 | 2/2009 | Ota |
| 2011/0304465 A1 | 12/2011 | Boult et al. |
| 2013/0035602 A1 | 2/2013 | Gemer |
| 2013/0305808 A1 | 11/2013 | Yoo |
| 2015/0084774 A1 | 3/2015 | Wojcik et al. |
| 2015/0325104 A1 | 11/2015 | Greenhut et al. |
| 2016/0231299 A1 | 8/2016 | Kang et al. |
| 2017/0166054 A1 | 6/2017 | Ayala Rodriguez et al. |

* cited by examiner

"30 minutes has passed. Test again to improve accuracy."

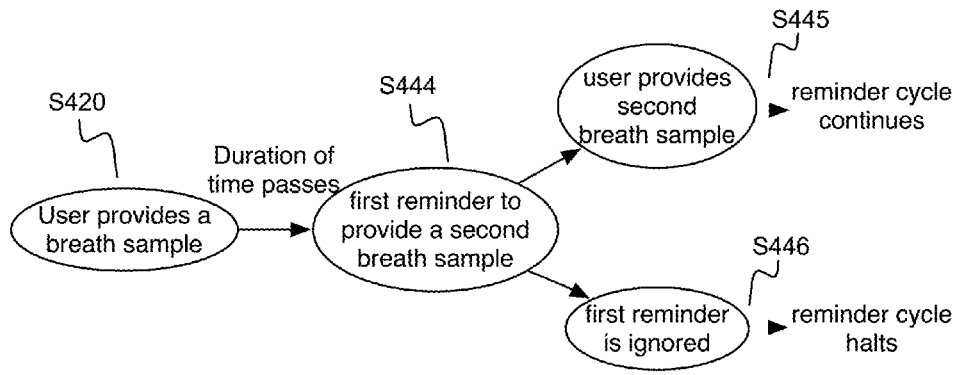
FIGURE 15
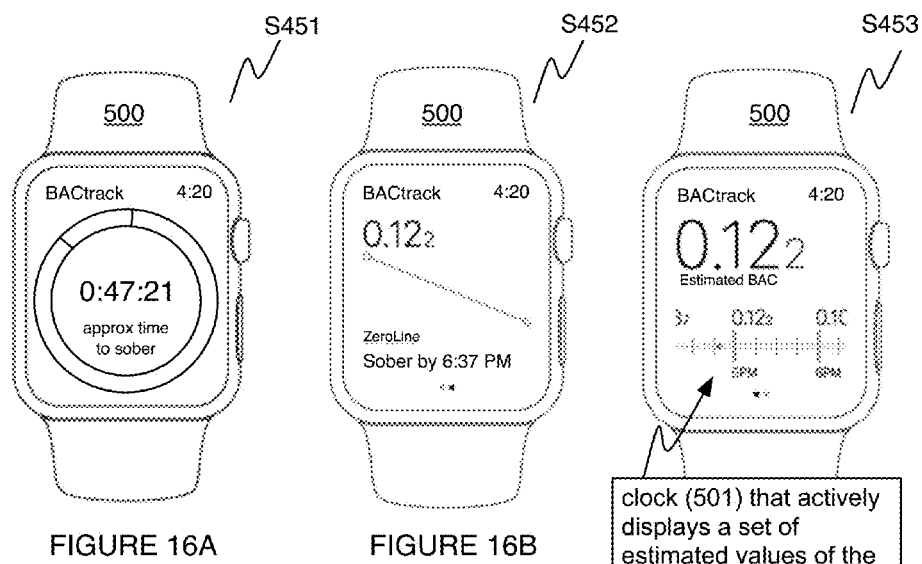
FIGURE 16A
FIGURE 16B
FIGURE 16C

METHOD AND SYSTEM FOR MONITORING INTOXICATION

CROSS-REFERENCE TO RELATED APPLICATIONS

This application is a continuation of U.S. application Ser. No. 15/294,317, filed 14 Oct. 2016, now U.S. Pat. No. 9,872,649, which is a continuation of U.S. Pat. No. 9,662,065, filed 28 Oct. 2015, which is a continuation of U.S. Pat. No. 9,192,334, filed 25 Feb. 2015, which is a continuation-in-part of U.S. Pat. No. 9,076,317 filed 27 Aug. 2014, which is a continuation of U.S. Pat. No. 8,878,669, filed 30 Jan. 2014, which claims the benefit of U.S. Provisional Application Ser. No. 61/812,704 filed 16 Apr. 2013 and U.S. Provisional application Ser. No. 61/759,390 filed 31 Jan. 2013, which are each incorporated in their entirety herein by this reference.

TECHNICAL FIELD

This invention relates generally to the intoxication monitoring device field, and more specifically to a new and useful method and system for monitoring intoxication.

BACKGROUND

It is often desirable to analyze a biological sample from a person to detect substances carried in the biological sample. As such, breathalyzer devices are used to test the content of alcohol (i.e., ethanol) carried in an individual's breath, in order to determine a measure of alcohol consumed by the individual. The measure is typically presented as a blood alcohol content (BAC), which can provide an indication of a user's mental and/or physical adeptness. As such, BAC measures are also used to provide a basis for limits of alcohol consumption in relation to the performance of tasks, including driving a vehicle, operating machinery, and performing various tasks in a working environment. While current blood alcohol measuring devices are able to determine an individual's BAC, and are typically used in law enforcement settings, existing systems and methods configured to provide monitoring of alcohol consumption are severely limited in both law enforcement settings and consumer device settings.

There is thus a need in the intoxication monitoring device field to create a new and useful method and system for monitoring intoxication. This invention provides such a new and useful method and system.

BRIEF DESCRIPTION OF THE FIGURES

FIG. 15 depicts a flowchart of an example of reminder provision, in an embodiment of a method for monitoring intoxication; and FIGS. 16A-16G depict examples of information provision to the user, at one or more mobile computing devices, in an embodiment of a method and system for monitoring intoxication.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Method

Figure 1A:
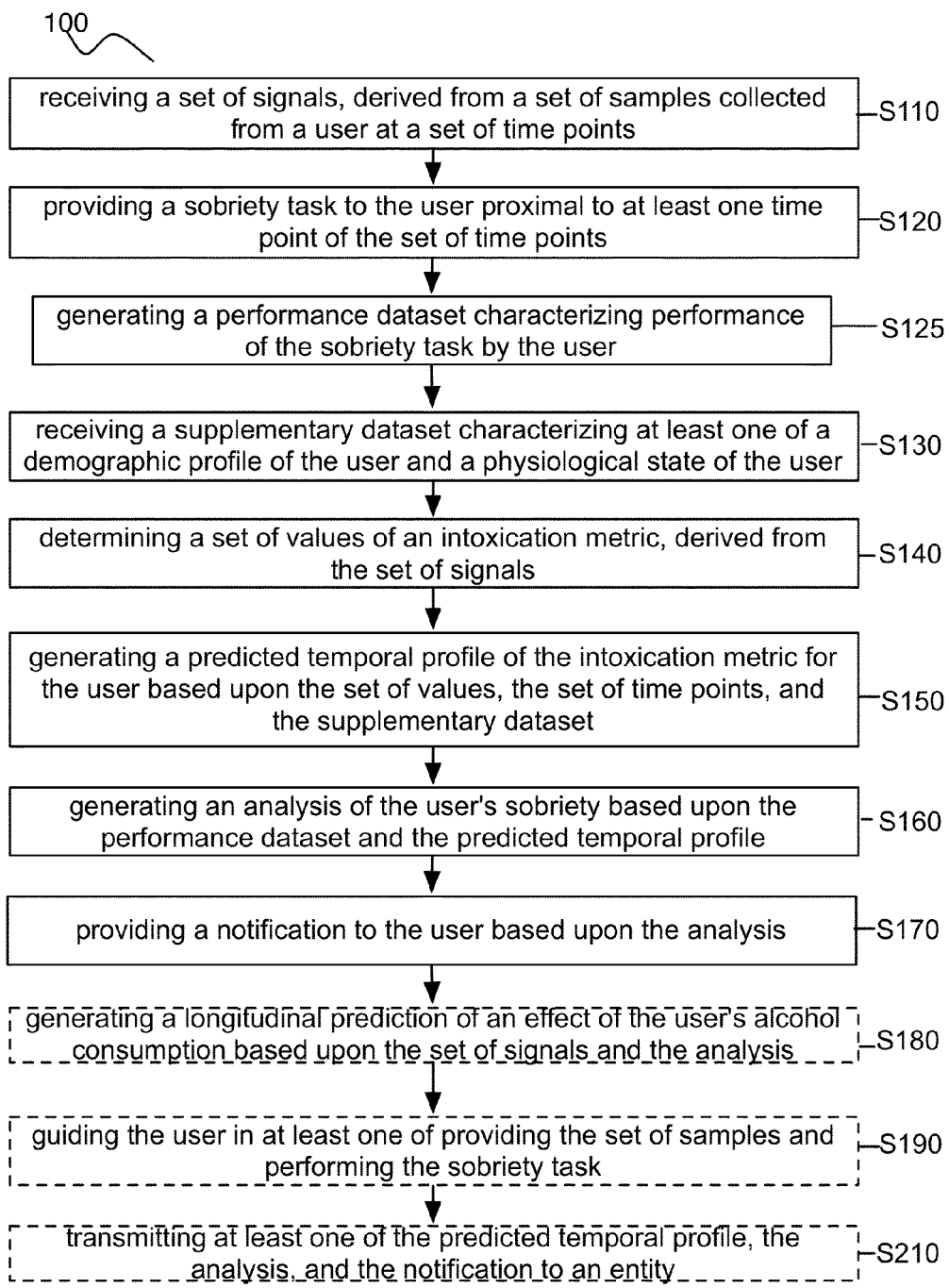
FIG. 1A depicts a schematic of an embodiment of a method for monitoring intoxication.

As shown in FIG. 1A, an embodiment of a method 100 for monitoring intoxication of a user includes: receiving a set of signals, derived from a set of samples collected from the user at a set of time points S110; providing a sobriety task to the user proximal to at least one time point of the set of time points S120; generating a performance dataset characterizing performance of the sobriety task by the user S125; receiving a supplementary dataset characterizing at least one of a demographic profile of the user and a physiological state of the user S130; determining a set of values of an intoxication metric, derived from the set of signals S140; generating a predicted temporal profile of the intoxication metric for the user based upon the set of values, the set of time points, and the supplementary dataset S150; generating an analysis of the user's sobriety based upon the performance dataset and the predicted temporal profile S160; and providing a notification to the user based upon the analysis S170. The method 100 can further comprise generating a longitudinal prediction of an effect of the user's alcohol consumption, based upon the set of signals and the analysis S180; guiding the user in at least one of providing the set of samples and performing the sobriety task S190; and transmitting at least one of the predicted temporal profile, the analysis, and the notification to an entity S210.

The method 100 functions to provide a tool that allows a user to monitor his/her alcohol consumption and behavioral effects of intoxication in a compelling and intuitive manner. The method 100 can also function to guide a user's behavior at various stages of intoxication, by providing notifications related to the user's intoxication state. In this regard, the method 100 can provide short-term and/or long-term predictions of a state of the user, in quantitative and qualitative manners, such that the user learns about the physiological and/or behavioral effects of his/her alcohol consumption. The method 100 can also incorporate a social component, wherein information related to a user's intoxication-induced behavior and/or physiological state can be communicated to another entity (e.g., a supervisor, a caretaker, a family member, an acquaintance).

Preferably, at least a subset of the method 100 is implemented using a portion of the system 200 described in Section 2 below, comprising a sample receiving module 210 configured to receive a set of samples from the user, a data link 248 configured to communicate signals derived from the set of samples, and a processing subsystem 250 configured to receive and process data in order to generate a notification that can be provided to the user at a user interface 205; however, the method 100 can be implemented using any other suitable system configured to collect and/or transmit samples from the user, analyze the samples, and provide information regarding the user's intoxication state. In one specific example, the method 100 is implemented at least in part using a breathalyzer unit including a wireless data link, a processing subsystem 250, and a mobile computing device 202 executing an application with a user interface 205 configured to receive inputs and provide information to the user. As such, the method 100 is preferably implemented for a user who is substantially removed from law enforcement personnel; however, the method 100 can alternatively be implemented for a user who is in proximity to law enforcement personnel.

In some embodiments, the method 100 can be adapted to actively inform a user of his/her intoxication state, by implementing features of a wearable mobile computing device in addition to or alternative to any other suitable mobile computing device(s). In particular, implementation of features of a wrist-borne mobile computing device and/or a head-mounted mobile computing device can allow a user to be actively informed of his/her sobriety in a manner that is less distracting and less obtrusive to the user (or entities in communication with the user) than traditional methods of notifying a user regarding his/her sobriety state. For instance, the method 100 can facilitate provision of information to the user at a wrist-borne or head-mounted mobile computing device having a display that the user can access or otherwise interact with to be provided with information pertaining to an intoxication state, without performing a distracting activity (e.g., reaching into a pocket or purse to interact with a mobile device). In these embodiments, the wrist-borne or head-mounted mobile computing device can be coupleable to another mobile device (e.g., as in an Apple Watch-iPhone connection, as in an Apple Watch-iPad connection, as in a Samsung Gear-Samsung smartphone connection, as in a Samsung Gear-Samsung tablet connection, as in an Android watch-Android smart device connection), wherein the other mobile device is coupleable to the sample reception module (e.g., by Bluetooth pairing); however, the wrist-borne or head-mounted mobile computing device can additionally or alternatively be coupleable directly to the sample reception module without an intermediate mobile device connection.

Figure 1B:
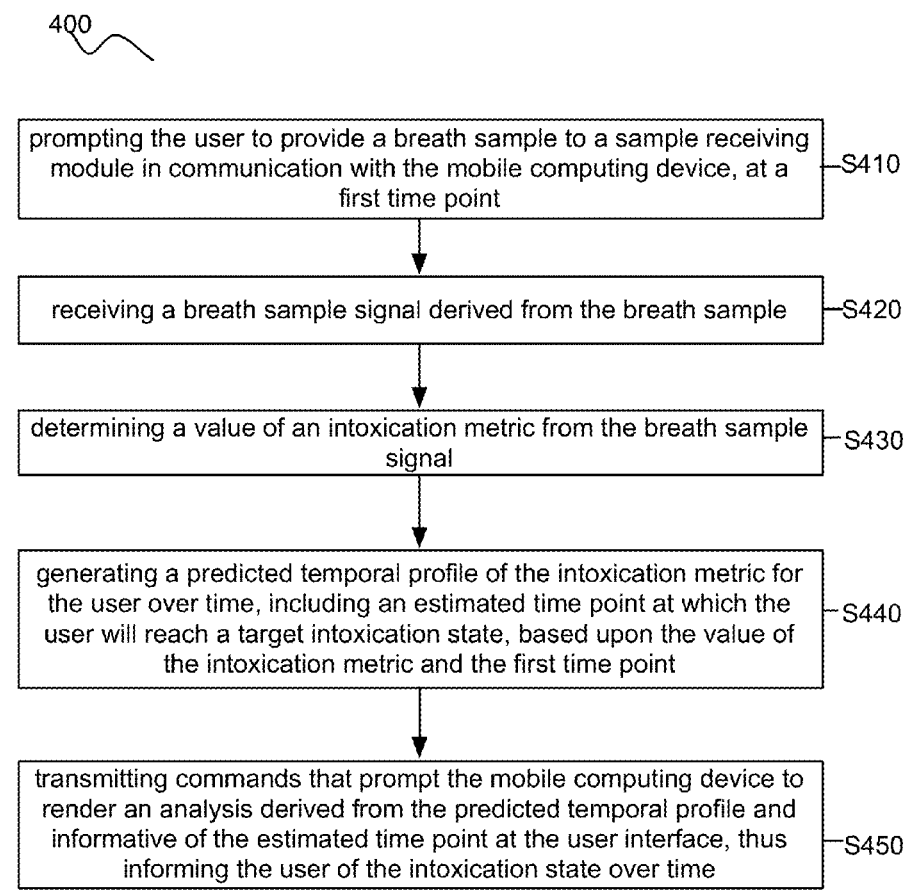
FIG. 1B depicts a flowchart schematic of an embodiment of a method for informing a user of an intoxication state.
Figure 1C:
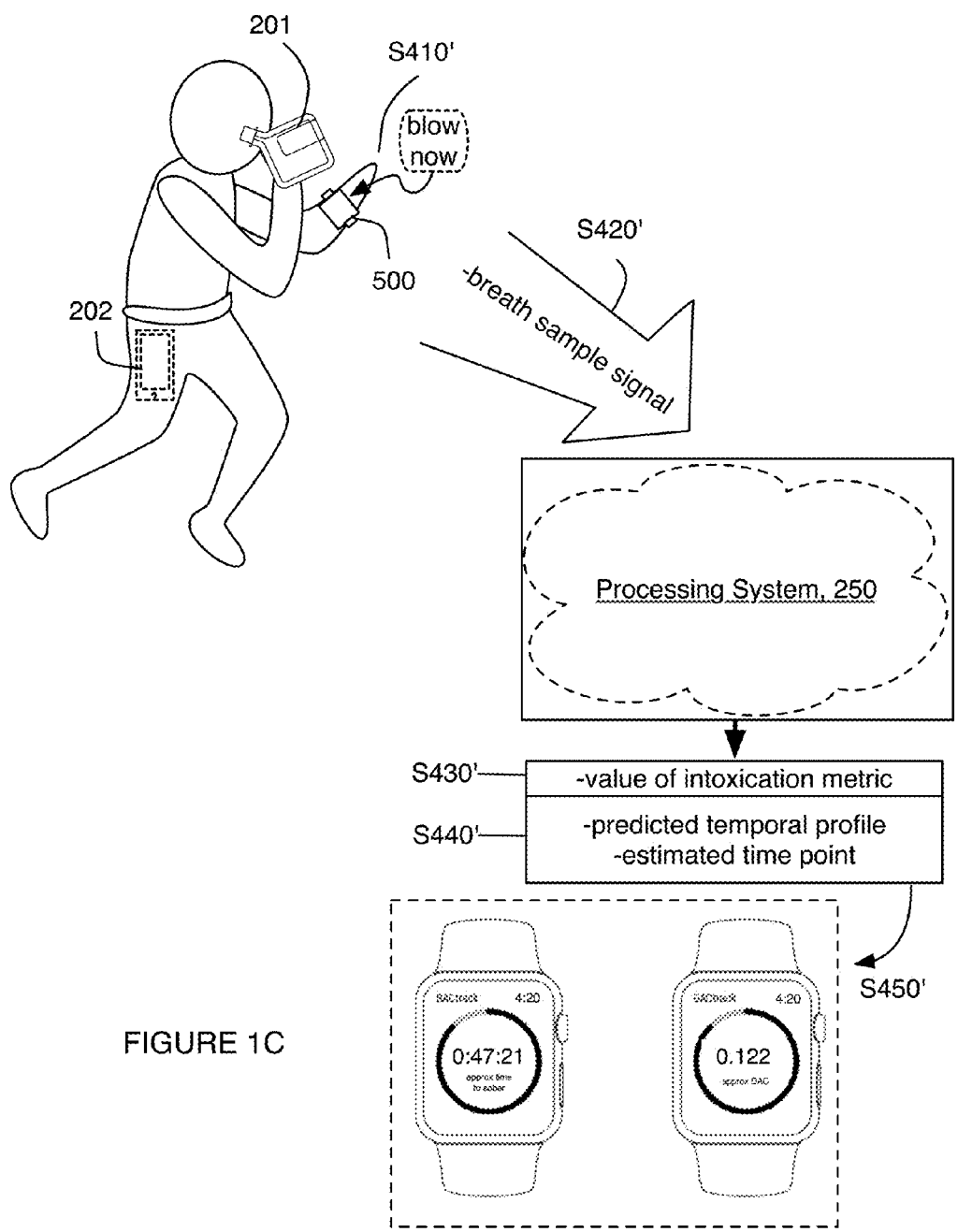
FIG. 1C depicts a schematic of an embodiment of a method for informing a user of an intoxication state.

In one such embodiment, as shown in FIGS. 1B and 1C, a method 400 for informing a user of an intoxication state comprises: using a mobile computing device associated with the user and having a user interface, prompting the user to provide a breath sample to a sample receiving module in communication with the mobile computing device, at a first time point S410; at a processing subsystem in communication with at least one of the mobile computing device and the sample receiving module, receiving a breath sample signal derived from the breath sample S420; at the processing subsystem, determining a value of an intoxication metric from the breath sample signal S430; at the processing subsystem, generating a predicted temporal profile of the intoxication metric for the user over time, including an estimated time point at which the user will reach a target intoxication state, based upon the value of the intoxication metric and the first time point S440; and transmitting commands that prompt the mobile computing device to render an analysis derived from the predicted temporal profile and informative of the estimated time point at the user interface, thus informing the user of the intoxication state over time S450. A schematic of the method 400, represented in Blocks S410', S420', S430', S440', and S450' is shown in FIG. 1C.

In this embodiment, the method 400 can thus allow the user to be actively informed of his/her intoxication state (e.g., estimated intoxication state, actual intoxication state) substantially in real-time or in near-real-time, and allow the user to understand when he/she will reach a target intoxication state (e.g., a state of sobriety, a state at which it is legal to drive, etc.) at a future time point. The method 400 can additionally or alternatively adapt estimates upon reception of one or more additional breath sample signals at one or more later time points, in coordination with reminding the user to provide one or more additional breath samples. In a specific example, the method 400 is implemented using an Apple Watch device to prompt the user to provide a breath sample and to inform the user of his/her intoxication state in a dynamic manner as time progresses; however, variations of the method 400 can additionally or alternatively be implemented using any other suitable wrist-borne mobile computing device (Samsung Gear, Android™ Wear device, etc.) and/or head-mounted mobile computing device (e.g., Google Glass, Vuvix device, etc.).

Block S110 recites: receiving a set of signals, derived from a set of samples collected from the user at a set of time points, and functions to enable generation of data that can be used to determine a predicted temporal profile of an intoxication metric. The set of signals is preferably received at processing subsystem, such as the processing subsystem described in Section 2 below; however, the set of signals can alternatively be received at any other suitable processing element configured to transform the set of signals into a set of values of an intoxication metric. Block S110 is preferably enabled using a sample receiving module (e.g., of a breathalyzer device) that is configured to collect the set of samples from the user. As such, the set of samples can be collected automatically and/or manually, can be collected continuously and/or intermittently, and can be collected at regular and/or irregular intervals. Furthermore, the set of samples can include any one or more of: breath samples (e.g., samples collected at a breathalyzer unit), urine samples, blood samples, interstitial fluid samples, and any other suitable sample that can be used to assess the user's intoxication.

Preferably, the set of samples is received from the user in Block S110 in a non-invasive manner; however, the set of samples can be received in a minimally invasive or invasive manner. Furthermore, in some variations, the set of signals can be received without directly collecting samples from the user; for example, the set of signals can be generated in an indirect manner, as derived from an interaction between a stimulus and the user's body (e.g., spectrometer-based analysis of light transmitted from a user's blood vessels). In still other variations, Block S110 can entirely omit using a set of samples from the user, and instead rely upon characteristics of the user and the user's alcohol consumption (e.g., gender, mass, number of drinks consumed, time over which the drinks have been consumed, etc.) to facilitate generation of values of an intoxication metric. In one such example, data used as inputs in a Widmark formula or a derivative thereof can be received in Block S110.

In a specific example of Block S110, the set of signals can be received wirelessly using a Bluetooth transmission module incorporated into a Breathalyzer unit configured to collect one or more breath samples from a user at one or more stages of intoxication. In the specific example, Block S110 can facilitate pairing between the Bluetooth transmission module of the Breathalyzer unit and a Bluetooth module of a computing device (e.g., a mobile computing device, a wrist-borne mobile computing device, a head-mounted mobile computing device, etc.). In more detail, pairing can be facilitated by way of an application executing on the mobile computing device and, upon establishing a connection between the Breathalyzer and the mobile computing device, the user can be provided with an option (i.e., a prompt) to provide an input that indicates that the user intends to provide a breath sample to the Breathalyzer. In the specific example, a sample of the set of samples can be collected at the breathalyzer unit prior to cessation of a period of alcohol consumption by the user, and/or a sample of the set of samples can be collected at the breathalyzer unit post-cessation of a period of alcohol consumption by the user. However, variations of the specific example can, however, involve pairing between devices (e.g., by WiFi, by a wired connection, etc.) and/or prompting of the user to provide a sample in any other suitable manner.

In relation to Blocks S410 and S420, receiving a breath sample signal is preferably performed in a manner similar to that described in relation to Block S110 above. In particular, in one variation, Block S410 can use a mobile computing device associated with the user and having a user interface, in prompting the user to provide a breath sample to a sample receiving module (e.g., of a Breathalyzer device). In this variation, a native application executing on the mobile computing device can facilitate establishment of communication (e.g., over a Bluetooth connection) between the mobile computing device and the sample receiving module, and can also guide the user in providing the breath sample at a first time point. In variations, guiding or prompting the user to provide the breath sample can comprise one or more of: visually guiding the user by rendering textual and/or graphical instructions at a display (e.g., of the mobile computing device, coupled to the sample receiving module, etc.); visually guiding the user by emitting light using a light emitting element (e.g., of the mobile computing device, coupled to the sample receiving module, etc.); audibly guiding the user by providing audio instructions through a speaker, (e.g., of the mobile computing device, coupled to the sample receiving module, etc.); haptically guiding the user by providing touch-sensitive feedback using an actuator/vibration motor (e.g., of the mobile computing device, coupled to the sample receiving module, etc.); and guiding in any other suitable manner.

In any of the above variations of guiding the user in Block S410, the user can be prompted to provide a breath sample after the user indicates that he/she is ready, for instance, by providing an input at an input module of the mobile computing device and/or the sample receiving module. In examples, providing the input can comprise one or more of: interacting with a touch sensitive display (e.g., by pushing, tapping, swiping, pinching, etc. a surface of the touch sensitive display), pressing a key/button, interacting with a microphone, activating a sensor (e.g., by shaking a device, by modulating an orientation or position of a device, etc.), by simply initiating provision of the breath sample (e.g., by blowing into the sample receiving module), and providing the input in any other suitable manner.

Furthermore, in relation to Block S420, a breath sample signal derived from the breath sample can be transmitted from the mobile computing device to a processing subsystem in communication with the mobile computing device (e.g., by connection to a remote server, in using on-board processing functions of the mobile computing device, by connection to a cloud computing platform, etc.). Additionally or alternatively, the breath sample signal can be received at the processing subsystem directly from the sample receiving module. However, reception of the breath sample and generation, provision, and reception of the breath sample signal derived from the breath sample can, however, be performed in any other suitable manner.

Figure 9:
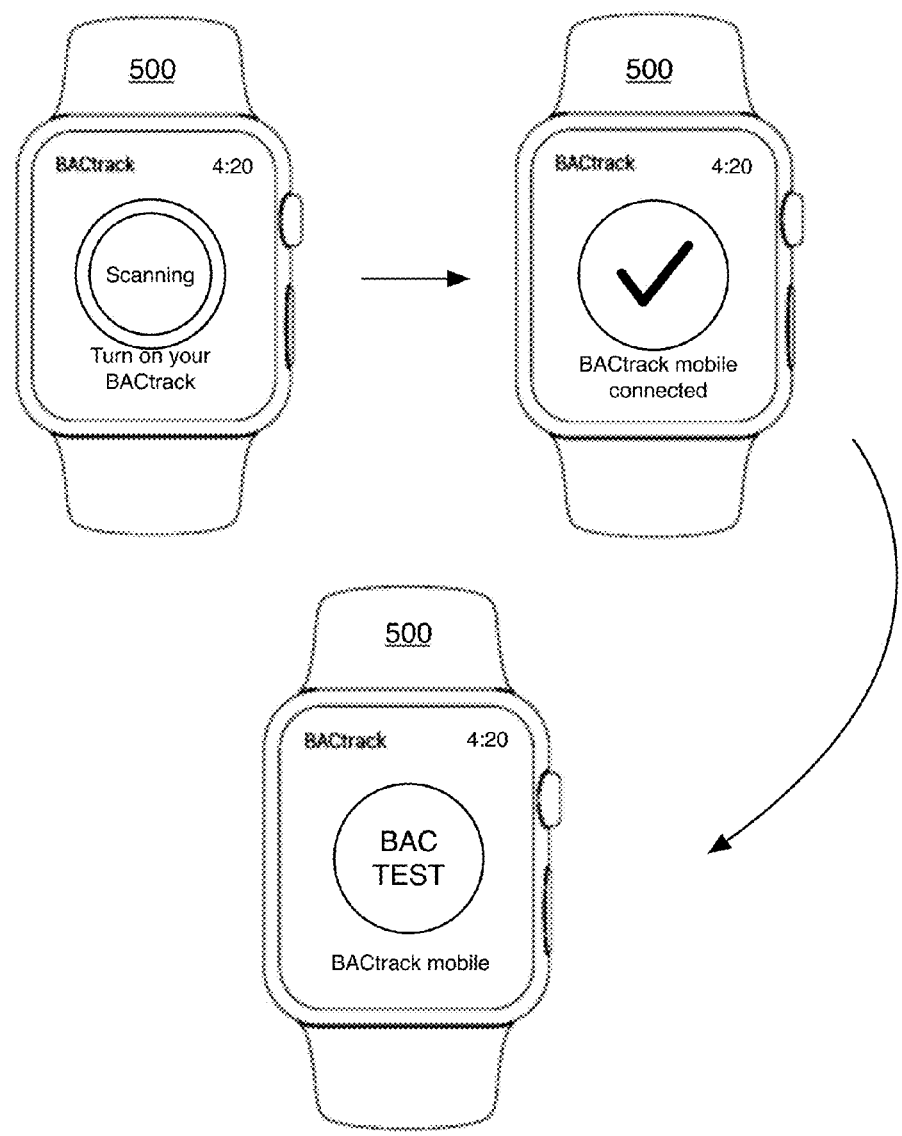
FIG. 9 depicts examples of device pairing in an embodiment of a method and system for monitoring intoxication.
Figure 10:
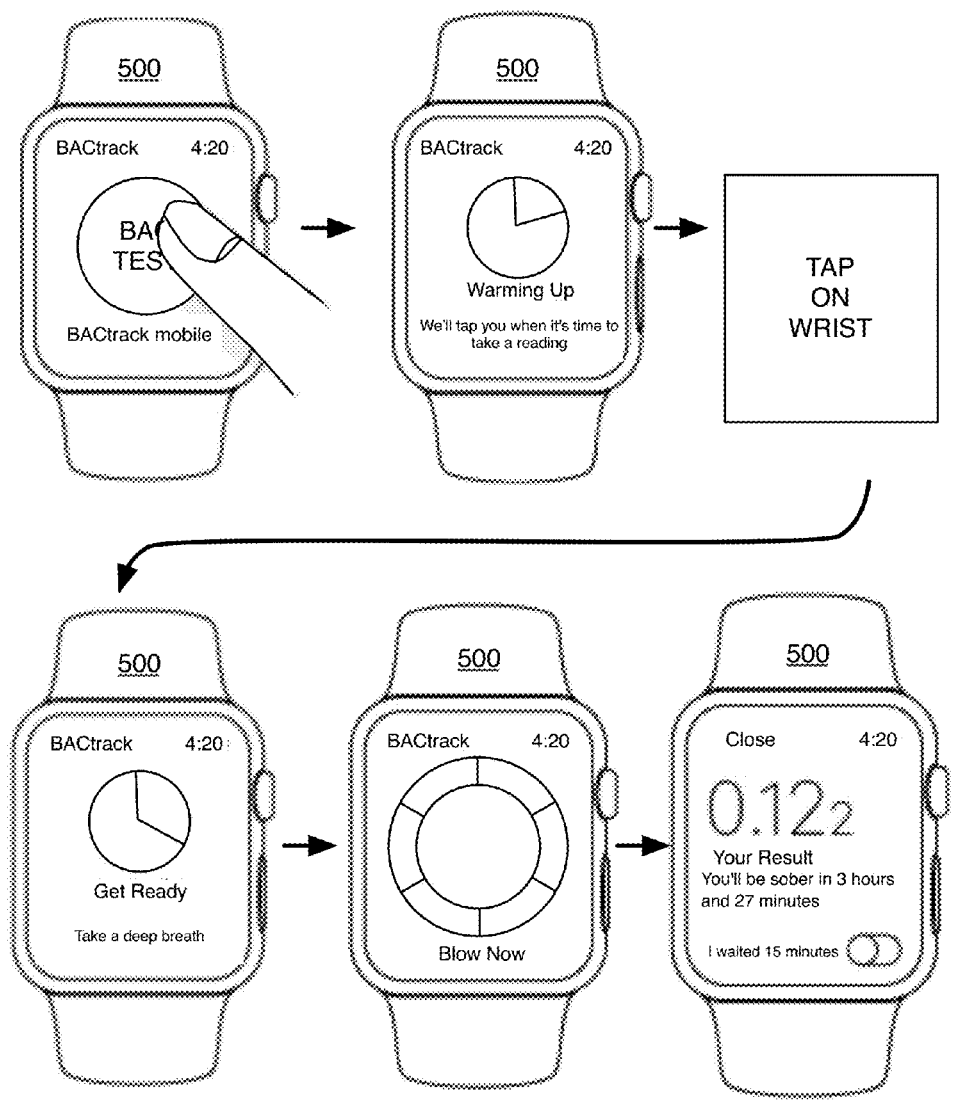
FIG. 10 depicts an example of user guidance in an embodiment of a method and system for monitoring intoxication.

In a specific example, Blocks S410 and S420 can facilitate pairing between a Bluetooth transmission module of the Breathalyzer unit and a Bluetooth module of a wrist-borne mobile computing device, as shown in FIG. 9. In more detail, pairing can be facilitated by way of a native application executing on the wrist-borne mobile computing device and, upon establishing a connection between the Breathalyzer and the mobile computing device, the user can be provided with an option (i.e., a prompt) to provide an input that indicates that the user intends to provide a breath sample to the Breathalyzer. In the specific example, as shown in FIG. 10, a touch-sensitive display of the wrist-borne mobile computing device can be used to render a graphic that the user can respond to with an input (e.g., by tapping the display, by pushing the display, etc.) to initiate provision of the breath sample. Then, as shown in FIG. 10, the native application can display one or more statuses (e.g., a warm-up status, an idling status, a ready status, etc.) of the sample receiving module, such that the user is informed regarding proper function of the sample receiving module. Finally, when the sample receiving module is ready to receive the breath sample, the native application executing at the wrist-borne mobile computing device can guide the user in providing the breath sample, by rendering a completion status meter at the display of the wrist-borne mobile computing device, as the user provides the breath sample. However, variations of the specific example of Block S410 and S420 can be implemented in any other suitable manner.

Block S120 recites: providing a sobriety task to the user proximal to at least one time point of the set of time points. Block S120 functions to enable an assessment of the user's abilities (e.g., motor ability, sensory ability, cognitive ability, etc.) associated with at least one state of intoxication, as determined from the set of samples collected from the user. The sobriety task is preferably provided to the user at a user interface in an electronic format, and in some variations, can be provided to the user at a user interface of a native application executing at an electronic device (e.g., mobile device) of the user. As such, the sobriety task is preferably implemented in a manner that incorporates functions enabled by sensors and components of the electronic device, including one or more of motion detection (e.g., by an accelerometer), location detection (e.g., by a GPS), audio detection (e.g., by a microphone), audio stimulation (e.g., by a speaker), visual stimulation (e.g., at a display), reaction time detection (e.g., by a user input module and a clock element), orientation detection (e.g., by a gyroscope), optical detection (e.g., at an optical sensor, at an image sensor), and any other suitable function. However, the motor skill task can alternatively be provided to the user in a non-electronic format (e.g., by a supervisor, by law enforcement personnel, by a caretaker, by a family member of the user, by an acquaintance of the user).

The sobriety task is preferably presented to the user proximal in time to each time point of the set of time points wherein the user provides a sample, such that performance of the sobriety task by the user can be directly associated with an intoxication metric derived from the sample. Furthermore the sobriety task can be provided to the user with at least one round of repetition, such that deviations between repeat performances and average performance metrics can be assessed. In examples, the sobriety task can be presented to the user in any one or more of the following configurations: prior to (e.g., immediately prior to) provision of a breath sample by the user at a breathalyzer, after (e.g., immediately after) provision of a breath sample by the user at a breathalyzer, and concurrently with provision of a breath sample by the user at a breathalyzer. However, in other variations, the sobriety task can additionally or alternatively be provided to the user substantially removed in time from a time point at which a sample is provided by the user, such that performance of the sobriety task by the user is not directly associated with an intoxication metric derived from a collected sample. In these variations, the user's performance of the sobriety task can, for example, be associated with a predicted value of an intoxication metric (e.g., from the predicted temporal profile generated in Block S150), or can, for example, be used to predict the value of an intoxication metric of the user without collection of a sample from the user.

The sobriety task can include a single task configured to enable an assessment of the user's abilities (e.g., motor ability, sensory ability, cognitive ability, etc.) associated with at least one state of intoxication, and in one variation, can include a test configured to gage a user's reaction to certain stimuli. In one example, the user can be presented with one or more stimuli (e.g., an audio stimulus, a visual stimulus, etc.), and the sobriety task can be used to assess the user's reaction (e.g., the user has a reaction response, the user does not have a reaction response) to the stimulus/stimuli. In another example, the user can be presented with one or more stimuli (e.g., an audio stimulus, a visual stimulus, etc.), and the sobriety task can be used to assess the user's reaction time to respond to the stimulus/stimuli. In another example, the user can be presented with a cognitive task (e.g., problem-solving task), and the user's ability to accomplish the cognitive task can be assessed in Block S160. In yet another example, the user can be presented with a cognitive task (e.g., problem-solving task), and the duration required by the user to accomplish the cognitive task can be assessed in Block S160. However, the sobriety task can additionally or alternatively include any other suitable task.

Figure 2:
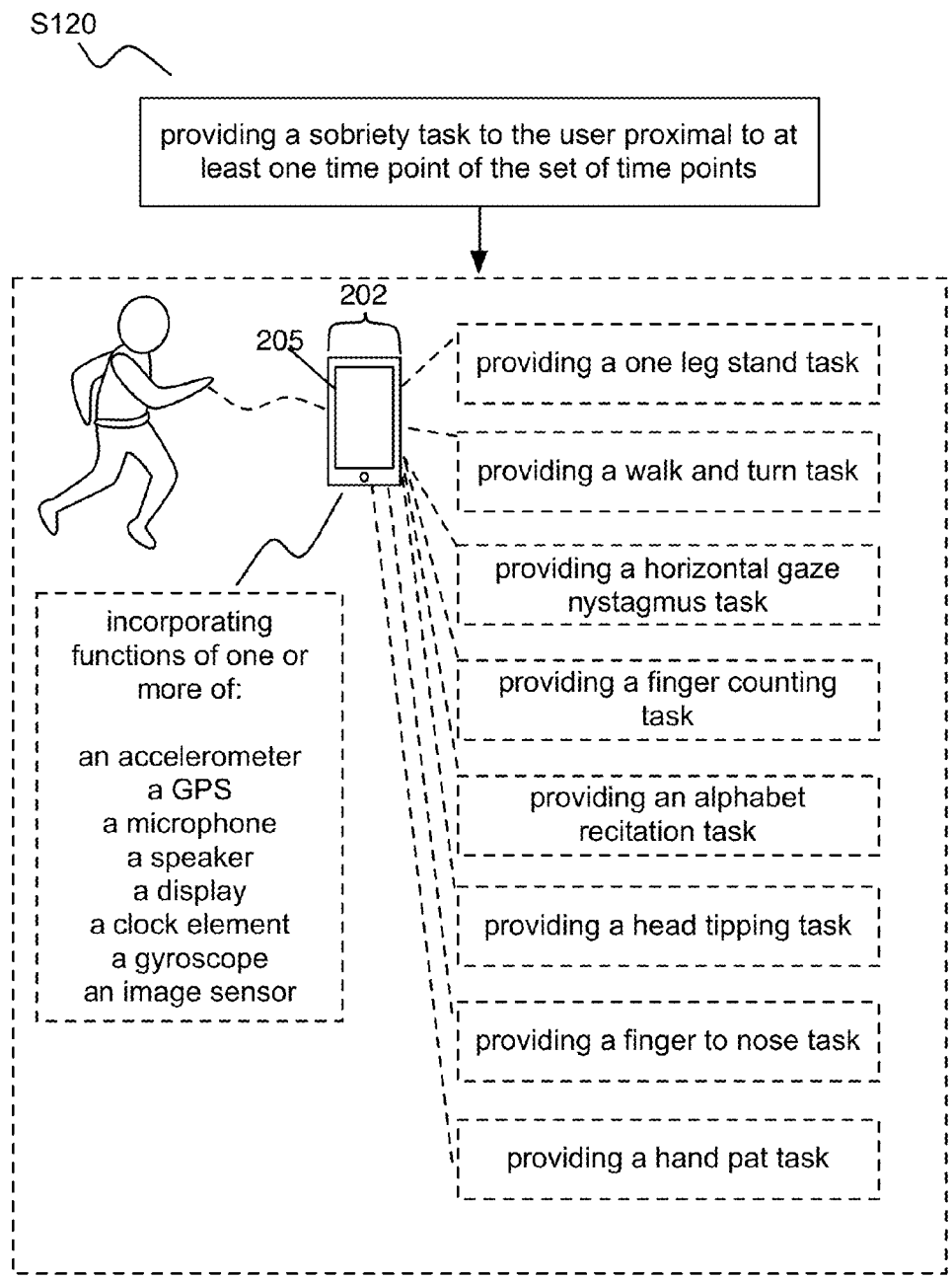
FIG. 2 depicts a schematic of a portion of an embodiment of a method for monitoring intoxication.

In other variations, the sobriety task can include a set of tasks, which can be provided in a consistent sequence whenever the user is provided with the sobriety task(s), in a random sequence, in an adaptive sequence (e.g., based upon the user's performance of a task of the set of tasks), and/or in any other suitable sequence. Furthermore, in embodiments wherein the sobriety task includes a set of tasks, the complete set of tasks can be provided to the user upon provision of the sobriety task to the user, or an incomplete set of tasks can be provided to the user, based upon a selection from the complete set of tasks by the user or by another entity. In some variations, as shown in FIG. 2, the set of tasks can be substantially identical to or analogous to tasks provided during a field sobriety test conducted by law enforcement personnel. In specific examples, the set of tasks can be configured to mimic field sobriety tests standardized by the National Highway Traffic and Safety Administration (NHTSA) of the United States of America, which include a one-leg stand (OLS) task, which requires a user to stand on one leg for 30 seconds to assess balance and coordination, a walk and turn (WAT) task, which assess a user's ability to balance and have his/her attention divided, and a horizontal gaze nystagmus (HGN) task, which assess involuntary jerking of the user's eye(s), indicative of intoxication. In variations of these examples, the set of tasks can additionally or alternatively include tasks configured to mimic tasks of any non-standardized sobriety tests, including one or more of: a finger counting (FC) task configured to assess cognition and vision, an alphabet recitation (AR) task, a counting task, a task wherein the user stands and slowly tips his/her head back, which enables an assessment of balance, a finger-to-nose (FTN) task configured to assess motor acuity, a hand-pat test, wherein the user alternatingly pats one hand with the palm and the back side of the other hand, and any other suitable task.

In specific examples, wherein a set of tasks configured to mimic a field sobriety test is provided using an application executing at a mobile device of the user, the set of tasks are implemented in a manner that incorporates functions enabled by sensors and components of the electronic device. In one example, the OLS task can incorporate image sensor functions, accelerometer functions, gyroscope functions, and/or clock functions to detect that the user is standing upon one leg (e.g., as enabled by the image sensor), and that the user has maintained balance for at least 30 sections (e.g., as enabled by the accelerometer, the gyroscope, and/or the clock). In another example, the WAT task can incorporate image sensor functions, accelerometer functions, and gyroscope functions to detect that the user is walking, is walking in a straight line, and is performing walking tasks according to instructions provided at a display and/or by the speaker of the mobile device. In another example, the HGN task can incorporate a moving visual stimulus at the display of the mobile device and optical sensor functions that track an eye of the user as the user visually follows the moving visual stimulus. In another example, the FC task can present a number of objects at the display of the mobile device, and the user can be instructed to identify and input the number of objects presented. In another example, the alphabet recitation task/counting task can instruct the user to recite a portion of the alphabet or count in any order, and a microphone of the mobile device can enable an assessment of the user's accuracy in reciting and/or counting. In yet another example, the FTN task can incorporate optical sensor functions, accelerometer functions, and gyroscope functions to detect the motion of the user as the user brings the mobile device in an outstretched hand to his/her nose, and has successfully performed the task (e.g., by the optical sensor).

Block S125 recites: generating a performance dataset characterizing performance of the sobriety task by the user, and functions to analyze the user's performance of the sobriety task. The performance dataset preferably characterizes the user's abilities (e.g., motor ability, sensory ability, cognitive ability, etc.) associated with at least one sample of the set of samples, in a quantitative manner. However, the performance dataset can additionally or alternatively characterize the user's abilities in a qualitative manner. As such, the performance dataset can include quantified values of aspects of the user's performance of the sobriety task, including one or more of: total response time (e.g., response time to complete a task), average response time across repeat performances of the sobriety task, deviation in response time between repeat performances of the sobriety task, total reaction time (e.g., reaction time to a stimulus), average reaction time across repeat performances of the sobriety task, deviation in reaction time between repeat performances of the sobriety task, and any other suitable quantified variable. Additionally or alternatively, the performance dataset can include qualitative aspects of the user's performance of the sobriety task, including one or more of: performance success (e.g., the user accomplished the task, the user did not accomplish the task), performance speed (e.g., fast, medium, slow), reaction response (e.g., user reacted, user did not react), and any other suitable qualitative characteristic. As such, the performance dataset provides data that can be used to analyze the user's sobriety in Block S160.

Block S130 recites: receiving a supplementary dataset characterizing at least one of a demographic profile of the user and a physiological state of the user, and functions to provide enriching data that can be used to increase the accuracy of the set of values of the intoxication metric determined in Block S140 and S430 and/or the predictive power of the predicted temporal profile generated in Block S150 and S440. The supplementary dataset is preferably received at processing subsystem, such as the processing subsystem described in Section 2 below; however, the supplementary dataset can alternatively be received at any other suitable processing element configured to use the supplementary dataset in generating a set of values of an intoxication metric. In Block S130, the demographic profile can include any one or more of information related to: gender (e.g., male, female, etc.), age, weight, height, ethnicity, marital status, profession, geographic location, diagnosed medical conditions (e.g., diabetes, alcohol intolerance), metabolic profile (e.g., fat/muscle content), family history, genetic information, and any other suitable type of demographic-related information. In Block S130, the physiological state of the user can be determined based upon any one or more of information related to: food consumption (e.g., amount/rate of consumption), beverage consumption (e.g., amount/rate of consumption), medication usage, activity (e.g., exercise, rest, sleep), biometric information (e.g., heart rate, respiration rate, pupilometric information, neural activity information, etc.), emotional state (e.g., stress state), and another other suitable type of physiological state-related information. The supplementary dataset can, however, include any other suitable type of data in addition to demographic data and/physiological state data.

The supplementary dataset received in Block S130 can be generated by manual input (e.g., by manual input from the user) and/or automatically based upon accessing of information databases relevant to the user. In variations wherein the supplementary dataset is generated by manual input, the user or another entity can manually input demographic information and/or information related to physiological state at a user input device, which is received as the supplementary dataset. In variations wherein the supplementary dataset is generated automatically, the supplementary dataset can be generated at an aggregation module configured to access, retrieve, and/or aggregate content (e.g., digital content) from different sources (e.g., social network accounts, search results, etc.). As an example, the supplementary dataset can be generated by an aggregation module configured to access and retrieve content from the user's Facebook, Twitter, and Instagram accounts, which can be used to provide demographic information, location information, and activity information (e.g., exercise regimen information, consumption information) related to a physiological state of the user. In another example, the supplementary dataset can be generated using a module configured to extract food and/or beverage consumption information (e.g., information pertaining to products intended to be consumed by the user, information from packages of products intended to be consumed or consumed by the user, etc.) from image and/or text data, for instance, using machine vision algorithms. The image and/or text data can be input by the user by way of an application executing at an electronic device (e.g., mobile device) of the user, wherein the electronic device comprises an image sensor; however, in variations of this example, the image data can additionally or alternatively be accessed and retrieved using an aggregation module in communication with the user's digital networks (e.g., digital social networks). As such, object recognition (e.g., of food items, of beverage items) and/or text recognition (e.g., of food labels, of drink labels) can be used to enable automatic identification of items that the user consumes, thus enriching the supplementary dataset. The image/text data can also be time stamped, such that the user's consumption activity can be associated in time with at least one time point of the set of time points, to facilitate generation of the predicted temporal profile in Block S150.

In the above examples and variations, the supplementary dataset preferably includes temporally static information (e.g., demographic information) and temporally varying information (e.g., physiological state information), but can include only temporally static information, only temporally varying information, and/or any other suitable type of information. Preferably, each piece of temporally varying information has an associated time stamp that is automatically retrieved and/or generated, such that the information can subsequently be associated with temporally varying intoxication states of the user predicted in variations of Block S150. However, the temporally varying information can additionally or alternatively be retroactively time-stamped (e.g., by a user, by another entity) in order to incorporate temporal information in the supplementary dataset.

Block S140 recites: determining a set of values of an intoxication metric, derived from the set of signals, and functions to determine at least one value of an intoxication metric that can be used to create one or more anchoring points for the predicted temporal profile generated in Block S150. The intoxication metric is preferably a blood alcohol content (BAC), which can be determined from signals generated from one or more of: a breath sample, a urine sample, a blood sample, and any other suitable biological sample from the user, as described in relation to Block S110 above; however, the intoxication metric can alternatively be any other suitable metric characterizing intoxication of the user. In variations wherein the set of signals is derived from breath samples of the user, a BAC value corresponding to each breath sample can be determined based upon the magnitude of an electrical signal produced when alcohol in the user's breath reacts with a sensing element of the sensor (e.g., a current magnitude produced by a platinum-alcohol oxidation reaction for a fuel cell sensor, a change in electrical resistance produced by an alcohol-dioxide reaction for a semiconductor sensor, etc.). In other variations, a BAC value corresponding to any other suitable type of sample from the user can be determined based upon an electrical signal produced in response to irradiation of the sample (e.g., by way of an electrical pulse generated in response to absorption of infrared light by the sample, using a spectrophotometer), by way of a detected chemical change (e.g., as exhibited by a color change) in response to a chemical reaction between the sample and a chemical additive, or in any other suitable manner.

In relation to Block S430, determining the value of the intoxication metric is preferably performed according to one of the variations and examples described in relation to Block S140 above, wherein determining the value of the intoxication metric comprises determining a value of a BAC of the user at the first time point. Preferably, the value of the BAC of the user is determined at the processing subsystem, and comprises analyzing a magnitude of an electrical signal (e.g., current magnitude, voltage magnitude, etc.) produced when alcohol in the user's breath reacts with a sensing element of the sensor (e.g., a current magnitude produced by a platinum-alcohol oxidation reaction for a fuel cell sensor, a change in electrical resistance produced by an alcohol-dioxide reaction for a semiconductor sensor, etc.). However, as described above, determining the value of the intoxication metric can additionally or alternatively be performed in any other suitable manner, and involve determination of a value of any other suitable intoxication metric from any other suitable type of sample from the user.

Figure 3A:
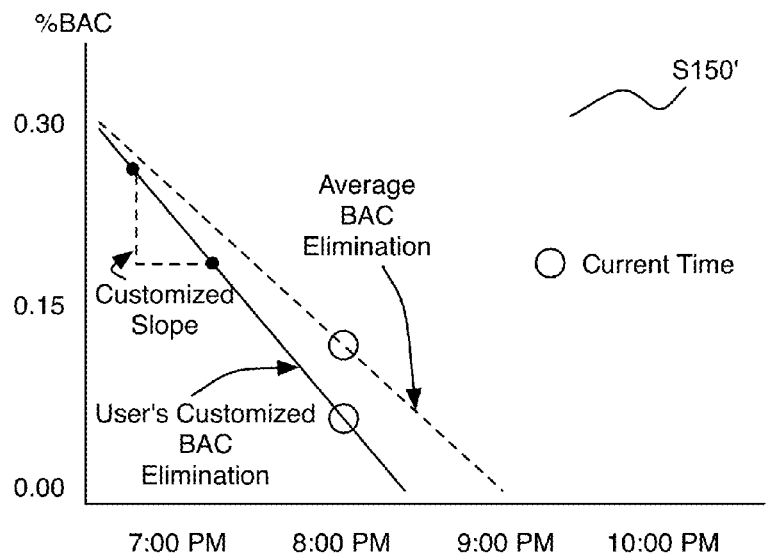
FIGS. 3A-3C depict embodiments of generating a predicted temporal profile that facilitates monitoring of the user's intoxication.

Block S150 recites: generating a predicted temporal profile of the intoxication metric for the user based upon the set of values, the set of time points, and the supplementary dataset, and functions to create a predicted temporal profile of an intoxication metric that is customized to the user and provides information regarding the user's past, present, and future states of intoxication in a quantitative and/or qualitative manner. Block S150 is preferably performed using an embodiment, variation, or example of the processing subsystem described in Section 2 below; however, Block S150 can additionally or alternatively be performed using any other suitable process system. When an individual consumes alcohol, their level of intoxication (e.g., as assessed by a BAC), will generally rise as alcohol is absorbed by their body, and then fall back to zero as alcohol is absorbed and processed by their body. As such, the predicted temporal profile characterizes an intoxication metric vs. time for the user, which can be used to predict when the intoxication metric for a user will reach a specific value at a point in time. The predicted temporal profile can thus be generated based upon one or more values of the set of values of the intoxication metric generated in Block S140 as anchoring points, as well as average profiles (e.g., rates) of alcohol absorption and elimination as determined previously from a population of individuals. Furthermore, generation of the predicted temporal profile can include forward and/or retrograde extrapolation of unknown future and/or past values of the intoxication metric, in relation to the set of values generated in Block S140. In an example, as shown in FIG. 3A, one value of an intoxication metric, determined for a time point after which the user has ceased alcohol consumption, can provide an anchoring point for a region of the predicted temporal profile over which the user's intoxication is declining, and average rates of alcohol elimination as determined from a population of individuals can be used to extrapolate the decline of the intoxication metric for the user over time, as depicted in the graphic labeled as S150' in FIG. 3A. Thus, if the user's BAC (i.e., the intoxication metric) is 0.03% at a first time point of the set of time points and an average elimination rate for a population of individuals is 0.015% per hour, the predicted temporal profile can characterize a decline in the user's BAC from 0.03% at the first time point to 0.00% two hours from the first time point. In another example, also shown in FIG. 3A, two values of an intoxication metric, determined for time points after which the user has ceased alcohol consumption, can be used to determine a slope for a region of the predicted temporal profile over which the user's intoxication is declining. Thus, if the user's BAC (i.e., the intoxication metric) is 0.05% at a first time point and 0.03% one hour after the first time point, the predicted temporal profile can characterize a decline in the user's BAC at a rate of 0.02% per hour, which is a customized rate for the user.

Figure 3B:
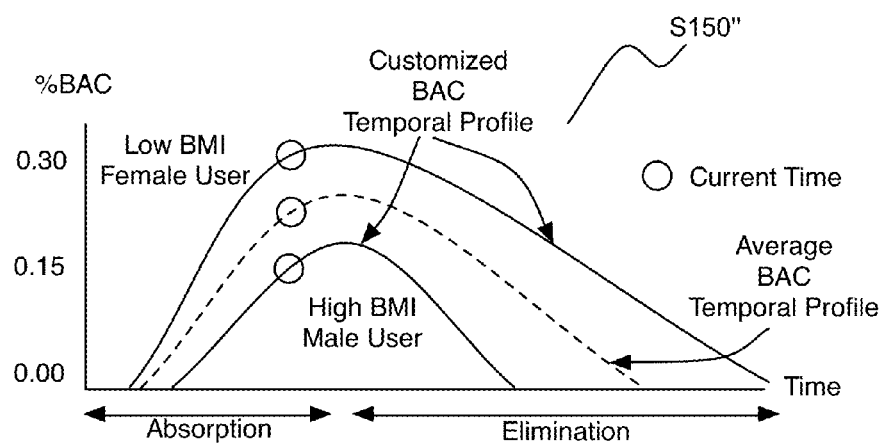

In the above variations and examples, the predicted temporal profile, including regions of rising, peaking, and declining intoxication, can further be adjusted and customized to the user, based upon the supplementary dataset. In variations, the user's alcohol absorption profile and/or elimination rate can be adjusted based upon the demographic profile of the user, as shown in FIG. 3B, as contained in the supplementary information. In one example, the predicted temporal profile can incorporate assumptions of a decreased alcohol absorption rate, an increased alcohol elimination rate and/or a BAC lower than average across all time points for a given number of alcoholic drinks consumed, given that the user is a male in his early 20's with a higher than average body mass index, a low fat-to-muscle ratio, and a family history of high tolerance to alcohol. In another example, the predicted temporal profile can incorporate assumptions of an increased alcohol absorption rate, a decreased alcohol elimination rate and/or a BAC higher than average across all time points for a given number of alcoholic drinks consumed, given that the user is a post-menopausal diabetic female with a lower than average body mass index, a high fat-to-muscle ratio, and a family history of low tolerance to alcohol. These examples are depicted in the graphic labeled as S150" in FIG. 3B. In another example, the predicted temporal profile can incorporate assumptions of an increased alcohol absorption rate, a decreased alcohol elimination rate and/or a BAC higher than average across all time points for a given number of alcoholic drinks consumed, given that the user has been diagnosed with any one or more of: deficiencies in alcohol dehydrogenase, deficiencies in aldehyde dehydrogenase, diabetes, hypertension, depression, and epilepsy. As such, the predicted temporal profile can be adjusted relative to a population average profile of intoxication characteristics, based upon specific demographic features of the user.

Figure 3C:
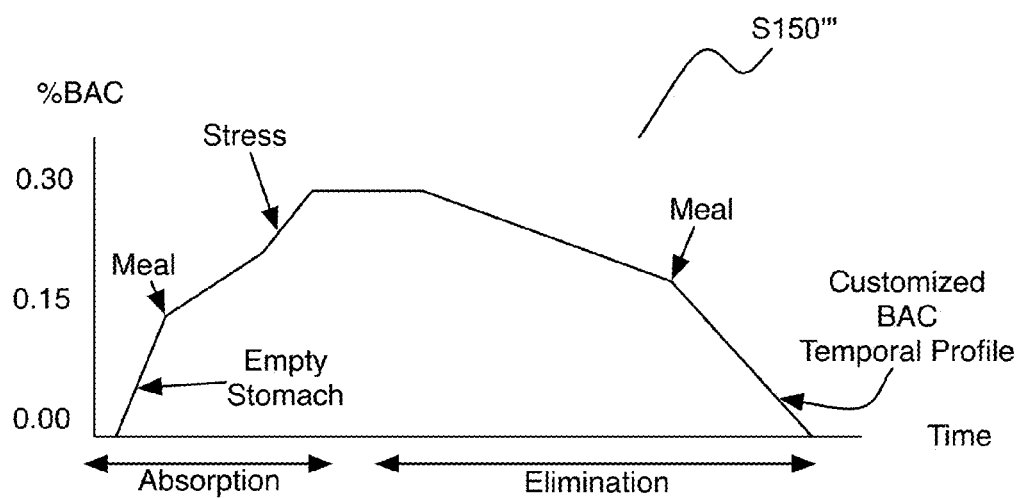

In variations of Block S150, the user's alcohol absorption profile and/or elimination rate can be additionally or alternatively adjusted based upon the user's physiological or metabolic state, as contained in the supplementary dataset. As such, as shown by the graphic labeled S150''' in FIG. 3C, data related to any one or more of: food consumption, beverage consumption, medication usage, activity, biometric information, emotional state, and any other suitable factor near a time point represented in the predicted temporal profile can be used to adjust an alcohol absorption profile and/or elimination rate. In one example, a region of rising intoxication in the predicted temporal profile can incorporate a decreased alcohol absorption rate and a lower peak BAC value post-consumption of a large meal, as identified within image data contributing to the supplementary dataset. In one example, a region of falling intoxication in the predicted temporal profile can incorporate an increased alcohol elimination rate post-consumption of a large meal, as identified within image data contributing to the supplementary dataset. In another example, a region of rising intoxication in the predicted temporal profile can incorporate an increased alcohol absorption rate and higher peak BAC value upon determination that the user is consuming alcohol on an empty stomach, as identified with the supplementary dataset (e.g., no images showing food consumption, no user input of information relating to a consumed meal, no check-ins at a food vendor location, GPS-based determination that the user has not visited a food vendor, etc.). In another example, a region of rising intoxication in the predicted temporal profile can incorporate an increased alcohol absorption rate and higher peak BAC value if the supplementary dataset includes biometric data indicating that the user is experiencing stress (e.g., fast heart rate, fast respiration rate, large pupil diameter, high neural activity, etc.). In another example, a region of rising intoxication in the predicted temporal profile can incorporate an increased alcohol absorption rate and higher peak BAC value if the supplementary dataset includes data indicating that the user has consumed carbonated beverages (e.g., as identified using image data).

In still other variations of Block S150, the user's alcohol absorption profile and/or elimination rate can be additionally or alternatively adjusted based upon reception and processing of additional breath sample signals, derived from additional breath samples provided by the user to the sample receiving module at time points after the first time point of breath sample provision. As such, the predicted temporal profile for the user can be dynamically adjusted as the processing subsystem receives and processes additional breath sample data, which can increase the accuracy of the predicted temporal profile as time progresses.

Figure 4:
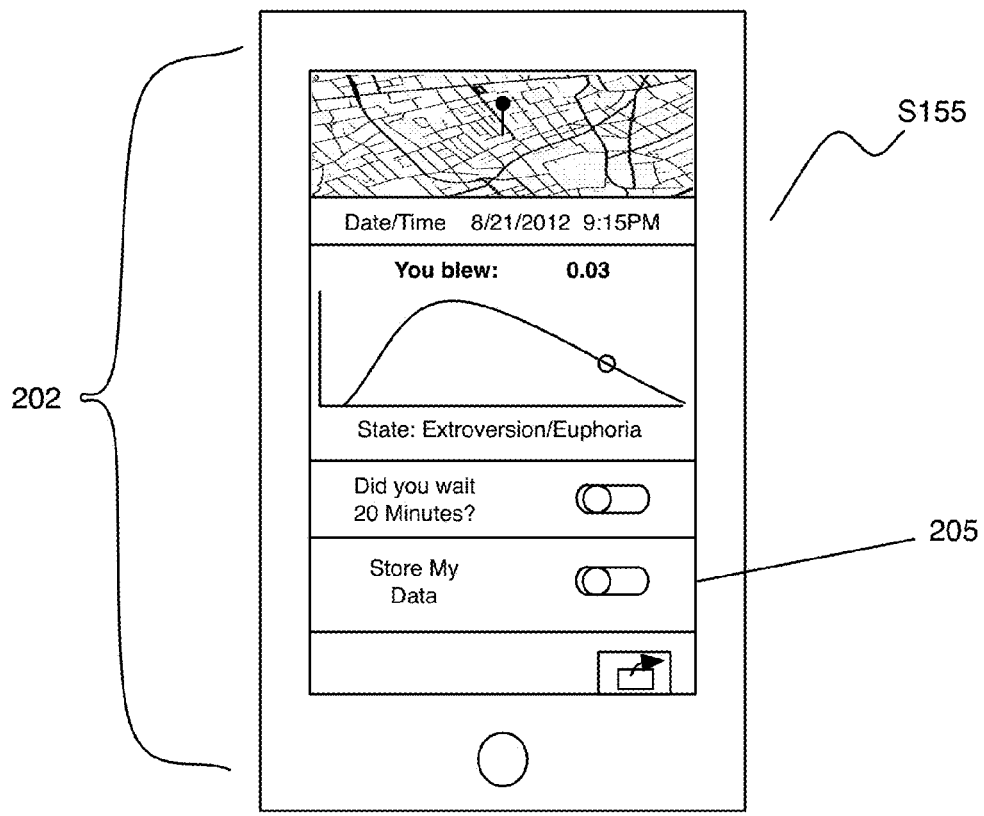
FIG. 4 depicts an example of an analysis, notification, and device/user interface configured to facilitate monitoring of the user's intoxication.
Figures 11A, 11B, 11C:
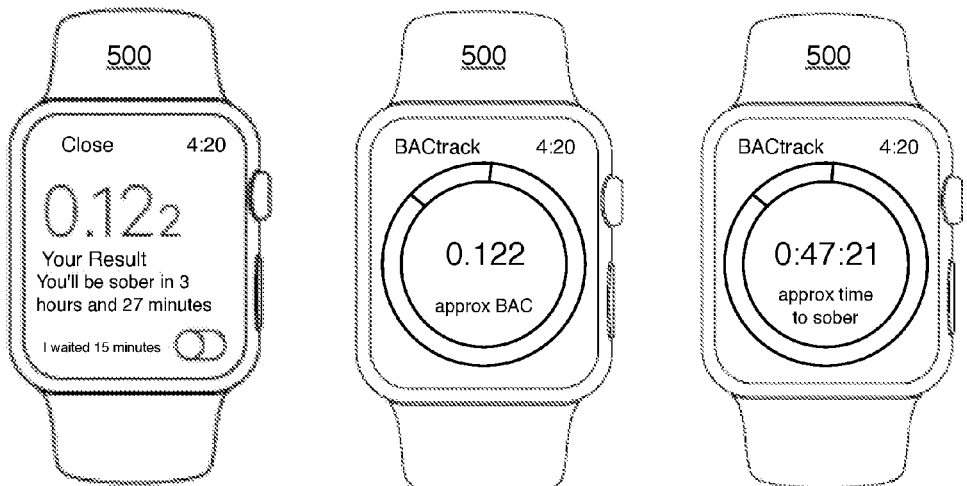
FIGS. 11A-11C depict examples of informing a user regarding his/her intoxication state, at a user interface of a wrist-borne mobile computing device, in an embodiment of a method for monitoring intoxication.

In any of the above variations and examples, customized aspects (e.g., elimination rates, absorption rates, intoxication peak characteristics, etc.) of the user's predicted temporal profile can be stored, used, and/or re-evaluated for future assessments of the user's intoxication. As such, a historical dataset (e.g., including at least one previously generated performance dataset and at least one previously generated predicted temporal profile) from the user can be used to refine predictions of alcohol absorption and/or elimination characteristics of the user, to increase the accuracy of the predicted temporal profile. In some variations, the method 100 can further include generating a prediction of a present value of the intoxication metric for the user, based upon the user's performance of the sobriety task (e.g., from the performance dataset). Thus, in an example, a user's score on the sobriety task can be used to determine an approximate current BAC value for the user, for instance, when the user is not near a sample receiving module. Furthermore, as shown in FIG. 4, the users predicted temporal profile can be rendered in some visual form (e.g., graphical form, text-based form), which can be provided to the user or other suitable entity (e.g., as part of Block S170) an example of which is labeled as S155 in FIG. 4. In one example, a predicted temporal profile of BAC vs. time, customized to the user, can be rendered as a line graph with selectable regions that associate future time points with predicted BAC values for the user. In other examples, some of which is shown in FIGS. 11A-11C, information derived from the predicted temporal profile of BAC vs. time can be rendered as a meter that indicates one or more of: a value of an intoxication metric derived from a breath sample provided by the user at a time point (FIG. 11A), an estimated value of the intoxication metric at a current and/or future time point (FIG. 11B), an estimated time point at which the user will reach a target intoxication state (e.g., a state of sobriety), a duration of time remaining until the user will reach a target intoxication state (e.g., a state of sobriety, as shown in FIG. 11C), and any other suitable information derived from the predicted temporal profile. The user's customized alcohol absorption and elimination rates can also be rendered or communicated, as well as any other suitable information.

In relation to Block S440, generating the predicted temporal profile of the intoxication metric is preferably performed as described in an embodiment, variation, or example of Block S150 above; however, the predicted temporal profile of the intoxication metric can additionally or alternatively be performed in any other suitable manner in Block S440. Furthermore, Block S440 is preferably implemented using an embodiment, variation, or example of the processing subsystem described in Section 2 below; however, Block S440 can additionally or alternatively be implemented in any other suitable manner. In Block S440, generation of the predicted temporal profile preferably includes generation of an estimated time point at which the user will reach a target intoxication state, based upon the value of the intoxication metric and the first time point, as well as one or more of an elimination rate and an absorption rate for the user.

Figure 12:
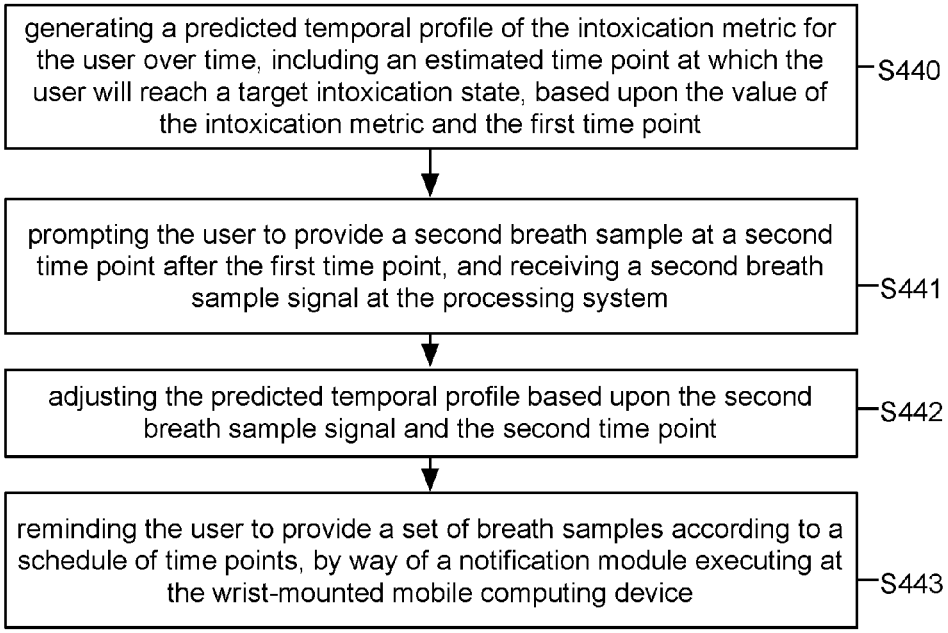
FIG. 12 depicts a flowchart schematic of a variations of a method for monitoring intoxication.

In variations of Block S440, generation of the estimated time point at which the user will reach the target intoxication state (e.g., a state of sobriety, a state at which it is legal to perform certain activities, etc.) can be implemented under the assumption that the user has ceased alcohol consumption; however, in other variations, generation of the estimated time point at which the user will reach the target intoxication state can be dynamically modulated in association with modulation of the predicted temporal profile, based upon reception and processing of additional information pertaining to behaviors of the user. For instance, Block S440 can include receiving a supplemental dataset comprising updated behavioral information of the user as time progresses, which can be used to modulate the estimated time point and/or the predicted temporal profile. In an example, the updated behavioral information can comprise information that indicates one or more time points associated with one or more alcohol consumption events of the user, and the predicted temporal profile can be adjusted accordingly to reflect a longer duration of time to reach the estimated time point. Furthermore, the updated behavioral information can be used as a trigger to prompt the user to provide another breath sample, in order to increase the accuracy of the estimated time point and predicted temporal profile in relation to an additional breath sample provided by the user. As such, and as shown in FIG. 12, Block S440 can further comprise Block S441, which recites: prompting the user to provide a second breath sample at a second time point after the first time point, and receiving a second breath sample signal at the processing system; and Block S442, which recites: adjusting the predicted temporal profile based upon the second breath sample signal and the second time point.

Additionally or alternatively, Block S440 can comprise allowing the user to provide an input at the mobile computing device (i.e., a wrist-borne mobile computing device, a head-mounted mobile computing device, a smartphone, a tablet, etc.) indicative of an intoxication-related behavior of the user, which can be used, by the processing system, to modulate estimation of the estimated time point at which the user will reach a target intoxication state, and or to modulate the predicted temporal profile. In this variation of Block S440, the input can be associated with one of a set of behaviors (e.g., consumption of one or more alcoholic beverages, consumption of one of a set of types of alcoholic beverages, exercise activity, eating activity, etc.). In an example, The input can be provided at an interface of a wrist-borne mobile computing device, wherein the user can indicate that he/she has consumed one drink at a specific time point later than a time point of the last provided breath sample. In this specific example, the input can comprise tapping a touch-display of the wrist-borne mobile computing device proximal a rendered icon that says "one drink" (indicating that the user has just consumed one drink), which adjusts the predicted temporal profile and estimated time point at which the user will reach a target intoxication state. Rendering of information provided to the user at the wrist-borne mobile computing device would then account for the adjustments to predictions based upon the user input. In variations of this specific example, the processing system can be trained to personalize the effect of one drink (or alternative intoxication-related behaviors) based upon historical data associated with the user, contextual (e.g., demographic information associated with the user, and/or an additional breath sample provided by the user after the user provides the input. For instance, the user's input of "one drink" can raise the user's currently estimated BAC in a predicted temporal profile by 0.02 if the user is a 150 lb male, and the user's input of "one drink" can raise the user's currently estimated BAC by 0.035 if the user is a 100 lb female.

In still other variations, Block S440 can include Block S443, which recites: reminding the user to provide a set of breath samples according to a schedule of time points, by way of a notification module executing at the wrist-borne mobile computing device. Block S443 functions to facilitate reception of a set of breath sample signals, distributed across a set of time points, which can increase the accuracy of the predicted temporal profile as time progresses. For instance, the set of breath samples can be used to automatically adjust the predicted temporal profile upon reception and processing of breath sample signals derived from the set of breath samples. In Block S443, the schedule of reminders can comprise regularly spaced time points, irregularly spaced time points, a desired number of time points, or any other suitable configuration of time points. Furthermore, the schedule of reminders can be automatically generated, or can additionally or alternatively be generated by a supervising entity (e.g., significant other, parole officer, parent, etc.) of the user, in variations of the method(s) 100, 400 involving remote monitoring of a user's alcohol consumption.

Figure 13:
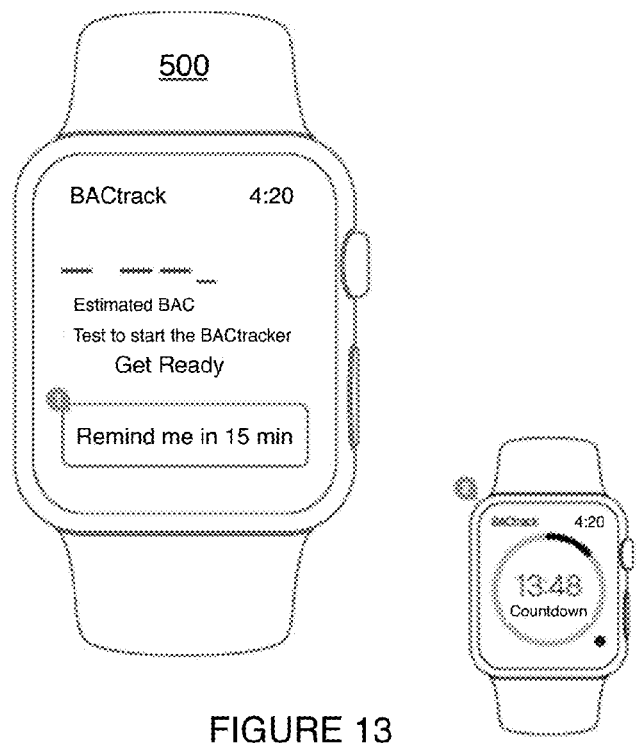
FIGS. 13 and 14 depict examples of reminder provision at a user interface of a wrist-borne mobile computing device, in an embodiment of a method for monitoring intoxication.
Figure 14:
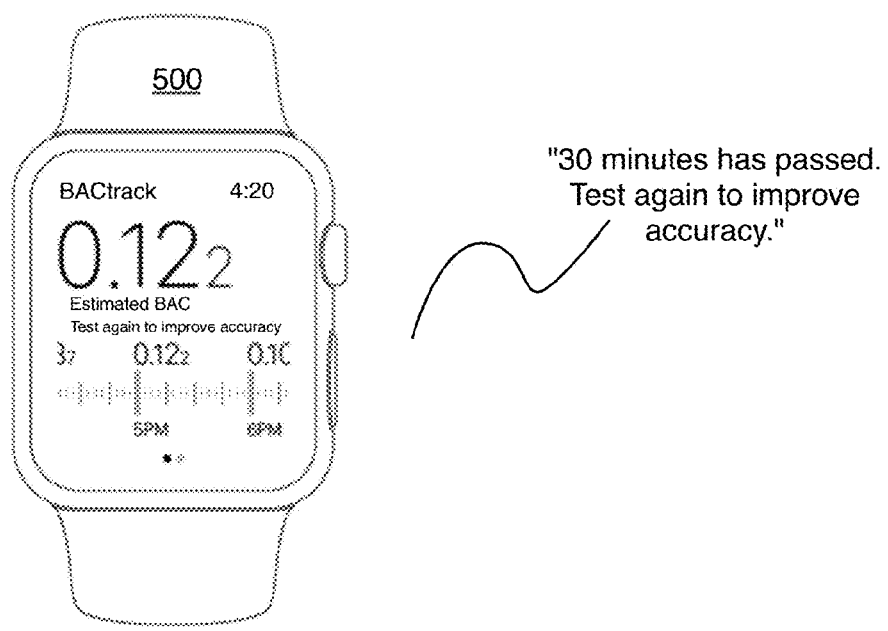

In Block S443, reminding the user can comprise one or more of: rendering a textual and/or graphical reminder at a display (e.g., of the mobile computing device, coupled to the sample receiving module, etc.); visually reminding the user by emitting light using a light emitting element (e.g., of the mobile computing device, coupled to the sample receiving module, etc.); audibly reminding the user by providing an audio output signal through a speaker, (e.g., of the mobile computing device, coupled to the sample receiving module, etc.); haptically reminding the user by providing touch-sensitive feedback using an actuator/vibration motor (e.g., of the mobile computing device, coupled to the sample receiving module, etc.); and reminding in any other suitable manner. In Block S443, provision of reminders according to the schedule can be initiated upon receiving an input that indicates that the user has opted for reminders to provide breath samples (an example of which is shown in FIG. 13). Additionally or alternatively, provision of reminders according to the schedule can be automatically performed upon detection that the user has entered an environment that provides alcohol (e.g., by using a GPS module of a mobile device associated with the user, upon detection that the user has checked-in at a location providing alcohol, etc.). Additionally or alternatively, provision of reminders can be initiated whenever a threshold duration of time has passed, during which the user has not provided a breath sample, as shown in FIG. 14. Additionally or alternatively, the user can opt for provision of a reminder at a desired future time point, based upon a factor that prevents the user from providing a suitable breath sample at a current time point. For instance, as shown in FIG. 13, if the user has just eaten or consumed alcohol, Block S443 can allow the user to opt for a reminder to provide a breath sample at a future time point (e.g., 15 minutes later, 20 minutes later, etc.) when provision of the breath sample is more suitable, in terms of reflecting an accurate representation of one's intoxication state. Additionally or alternatively, provision of reminders in Block S443 can be triggered or initiated in any other suitable manner.

In one variation, as shown in FIG. 15, Block S443 can comprise reminding the user to provide a set of breath samples according to the schedule of time points, wherein, in a first mode, if the user responds positively to a reminder and provides a subsequent breath sample, providing reminders according to the schedule of reminders continues. Alternatively in a second mode, if the user ignores a reminder and fails to provide a breath sample, providing reminders according to the schedule of reminders ceases for at least a period of time, in the interest of not over-engaging the user. However, once the user ignores a reminder, a warning message (e.g., a message that informs the user that provision of a breath sample will increase accuracy of information provided to the user) can be rendered at a device associated with the user, an example of which is shown in FIG. 14. In some extensions of this variation, ignoring of a reminder by the user can be used as a trigger to access additional information pertaining to behaviors, locations, and/or statuses of the user, wherein if the additional information indicates that the user is in a compromised state, help can be provided to the user. In one such example, a processing system associated with the system can send a taxicab to the user's location, and facilitate delivery of the user to his/her home in a safe manner. Additionally or alternatively, in relation to a predicted temporal profile or a trigger state, the user (or another entity) can provide an input that indicates a critical intoxication state at which he/she desires intervention (e.g., in the form of a ride home), and the processing system can be configured to process the input and facilitate achievement of the intervention when the critical intoxication state is reached by the user. In a specific example, the user can thus indicate at an interface of a native application that he/she would like to be picked up when his/her BAC is above 0.05, and the processing system can initiate sending of a car-ride service to his/her location. In these variations or examples, a third party (e.g., entity associated with the user, caretaker of the user) can be provided with a bill for the car-ride service if the user's intoxication state is above a certain threshold (e.g., the user is incapacitated).

Block S160 recites: generating an analysis of the user's sobriety based upon the performance dataset and the predicted temporal profile, and functions to provide a customized analysis of the user's past, present, and/or future intoxication state(s), so that the user is able to effectively monitor his/her intoxication. The analysis preferably incorporates the predicted temporal profile, with a distribution of the intoxication metric for the user over a given time window. The analysis also preferably includes an assessment of the user's performance of the sobriety task, as determined from the performance dataset, which can be represented as one or more scores that represent the user's performance of the sobriety task at time points captured in the predicted temporal profile. For each relevant time point, the score(s) generated from the performance dataset are preferably based upon one or more of: a total response time (e.g., response time to complete a task) to complete the sobriety task, an average response time across repeat performances of the sobriety task, a deviation in response time between repeat performances of the sobriety task, a total reaction time (e.g., reaction time to a stimulus of the sobriety task), an average reaction time across repeat performances of the sobriety task, a deviation in reaction time between repeat performances of the sobriety task, and any other suitable quantified variable. Additionally or alternatively, the score(s) generated from the performance dataset can be based upon one or more of: a qualitative measure of performance success (e.g., the user accomplished the task, the user did not accomplish the task) converted to a binary score (e.g., 1=accomplishment, 0=failure), performance speed (e.g., fast, medium, slow) converted to a quantization (e.g., fast to slow performance mapped on a 1-10 scale), reaction response (e.g., user reacted, user did not react) converted to a binary score, and any other suitable factor. Thus, for at least one point on the predicted temporal profile, the analysis provides a sobriety task score that associates the user's abilities, as assessed by the sobriety task, with an intoxication state as assessed by the intoxication metric.

Figure 5A:
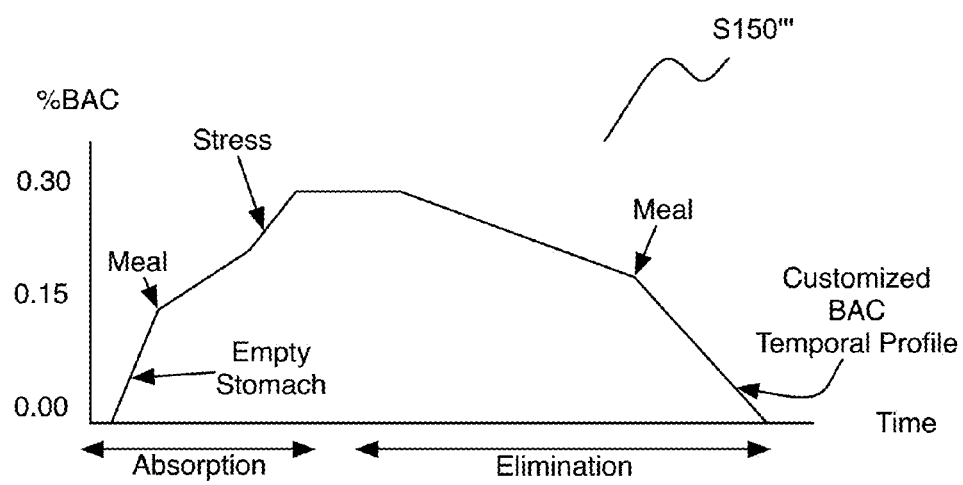
FIGS. 5A-5B depict examples of an analysis configured to facilitate monitoring of the user's intoxication.
Figure 5B:
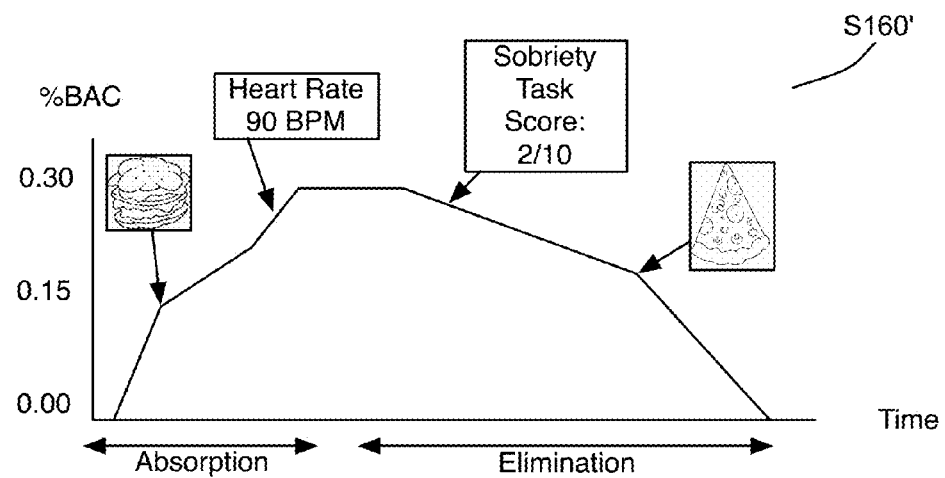

In Block S160, the analysis can also associate or annotate data points along the predicted temporal profile with user activities (e.g., meal consumption details and times, beverage consumption details and times, biometric data events, exercise events, medication events, rest events, etc.), as provided within the supplementary dataset or other suitable source. In one example, image and/or text data (e.g., images of meals, images of beverages, status updates, etc.) of the supplementary dataset can be used to annotate the predicted temporal profile, as shown in FIGS. 5A-5B, based upon time stamps of the image and/or text data, as depicted by the graphic labeled S160' in FIG. 5B. Furthermore, the analysis can be rendered in any suitable manner (e.g., tabulated format, graphical format, textual format, audio format, etc.) at a user interface or other interface, such that the comprehensive analysis is provided to the user and/or another entity. Additionally, the analysis or a derivative of the analysis can be co-presented with assumptions and factors (e.g., demographic factors, physiological state factors, etc.) used to customize the analysis to the user.

Block S170 recites: providing a notification to the user based upon the analysis, and functions to provide an alert, recommendation, and/or information that informs the user of an effect of intoxication on his/her present or future behavior. The notification can include a notification of any suitable type (e.g., visual notification, haptic notification, audio notification, etc.), and can be provided to the user in any suitable manner (e.g., using a messaging client accessible by the user, at a mobile device of the user, by a supervisor of the user, etc.). The notification can be provided automatically based upon a given alert state (e.g., an automated notification upon detection that the user is entering a dangerous intoxication state), and/or can be provided when prompted by the user or other entity. The notification preferably informs the user of his/her current intoxication state, as shown in FIG. 4, which in examples informs the user that he or she is: currently above a legal limit of intoxication (e.g., for operating a vehicle), currently below a legal limit of intoxication, or currently at an unknown intoxication state relative to a legal limit of intoxication. In further examples, the notification can inform the user that he or she is: currently below a legal limit of intoxication, but should not perform relevant activities (e.g., operating a vehicle, operating machinery) due to poor performance of the sobriety task, currently at an unknown intoxication state relative to a legal limit of intoxication, but should not perform relevant activities (e.g., operating a vehicle, operating machinery) due to poor performance of the sobriety task, or currently above a legal limit of intoxication and should not perform relevant activities, even though the user has performed the sobriety task well.

The notification can additionally or alternatively inform the user of a predicted future intoxication state, which, in examples informs the user that he or she will be: above a legal limit of intoxication (e.g., for operating a vehicle) at a future time point, below a legal limit of intoxication at a future time point, or at an unknown intoxication state relative to a legal limit of intoxication at a future time point. Furthermore, the notification regarding a predicted future intoxication state can be governed by an input from the user or other entity. As such, in variations, Block S160 can include allowing the user to input a request for information regarding a future intoxication state, and providing the notification based upon the request. In one example, a user can thus request information for when his/her BAC will return to zero (or any other suitable value), and the notification can provide an answer with or without a degree of certainty in the prediction. In another example, the user can request information regarding an effect of a consumed meal or beverage on his/her intoxication at a future time point, and the notification can provide an answer (e.g., a predicted BAC value at the future time point) with or without a degree of certainty in the prediction.

The notification can additionally or alternatively inform the user of an analyzed past intoxication state, which, in examples informs the user that he or she was: above a legal limit of intoxication (e.g., for operating a vehicle) at a past time point, below a legal limit of intoxication at a past time point, or at an unknown intoxication state relative to a legal limit of intoxication at a past time point. The notification can also be coupled with contextual information for the past time point, such as information provided in the supplementary dataset. In one example, the notification can inform the user of a BAC level at a past time point, and the location of the user when the user demonstrated the BAC level, which can help the user identify the location at which he/she lost an item in a state of inebriation. In another example, the notification can inform the user of a BAC level at a past time point, and an activity of the user (e.g., exercise activity, stress state, medication state), when the user demonstrated the BAC level, which can help the user identify correlations between the user's activities and the user's intoxication states.

The notification can additionally or alternatively indicate past, current, and/or future alcohol-induced behavior and/or impairment of the user. In variations, the notification can provide a BAC value for a past, current, or future time point, along with typical behavior and/or impairment information. In examples of these variations, the notification can include one or more of: an identified BAC in the range of 0.010-0.029, which produces normal behavior and subtle impairment effects; an identified BAC in the range of 0.030-0.059, which produces mild euphoria, relaxation, joyousness, talkativeness, decreased inhibition, and impairment of the user's concentration; an identified BAC in the range of 0.060-0.090, which produces blunted feelings, disinhibition, extroversion, impairment of reasoning, impairment of depth perception, impairment of peripheral vision, and impairment of glare recovery; an identified BAC in the range of 0.100-

0.190, which produces over-expression, emotional swings, anger, sadness, boisterousness, decreased libido, impairment of reflexes, impairment of reaction time, impairment of gross motor control, impairment of speech, erectile dysfunction, and alcohol poisoning; an identified BAC in the range of 0.200-0.290, which produces stupor, loss of understanding, impaired sensations, possibility of falling unconscious, severe motor impairment, loss of consciousness, and blackout; an identified BAC in the range of 0.300-0.390, which produces severe central nervous system depression, unconsciousness, possibility of death, bladder dysfunction, breathing impairment, and disequilibrium; an identified BAC in the range of 0.400-0.50, which produces general lack of behavior, unconsciousness, possibility of death, breathing impairment, and nystagmus; and an identified BAC greater than 0.500, which produces high risk of poisoning, and possibility of death.

In some variations, Block S170 can further include enabling the user to provide an input indicative of an estimated intoxication state of the user S171, generating a comparison between the estimated intoxication state of the user and an actual intoxication state of the user (e.g., as derived from a breath sample provided by the user proximal in time to the time point at which the user indicates the estimated intoxication state) S172, and providing a notification to the user, wherein the notification is configured to facilitate convergence of the estimated intoxication state and the actual intoxication state S173 in instances of future alcohol consumption. Blocks S171, S172, and S173 function to train the user in becoming more aware of his/her actual intoxication state, such that the user can more effectively estimate his/her intoxication levels during alcohol consumption. The estimated intoxication state and/or the actual intoxication state can be a past, present, or future intoxication state, such that the user can be trained to estimate past, present, and/or future states of intoxication during alcohol consumption.

In Block S171, the input is preferably provided by the user by way of an application executing at a mobile device of the user, wherein the mobile device is in communication with a processing module configured to analyze the input in relation to the actual intoxication state of the user. However, in Block S171 the input can be received by way of an input module coupled to or integrated with a system for monitoring respiration, as described in Section 2 below, and/or in any other suitable manner. In variations, Block S171 includes allowing the user to provide an estimated BAC level (e.g., past, present, or predicted future BAC level); however, any other quantitative or qualitative estimated intoxication state (e.g., cognitive ability, motor skill ability, etc.) can be provided in other variations of Block S171. The comparison generated in Block S172 preferably calculates a difference between the estimated and the actual intoxication states of the user; however, the comparison can additionally or alternatively calculate any other suitable metric (e.g., a change in difference between estimated and actual intoxication state, relative to at least one past estimate of intoxication state) configured to train the user in identifying his/her actual intoxication state at a given state in time. In Block S173, the notification can be provided to the user in any one or more of: a visual manner (e.g., at a display), a haptic manner (e.g., using a vibration motor), an auditory manner (e.g., using a speaker), and in any other suitable manner that indicates the user's level of success in predicting his/her intoxication state. In specific applications, Blocks S171-S173 can enable the user to input an estimate of his/her BAC at an input module (e.g., keyboard, touchpad, touchscreen, voice recognition module, etc.) of a mobile device included in or coupled to system for monitoring intoxication, and providing the notification at a display of the mobile device in a visual manner.

Figure 16D:
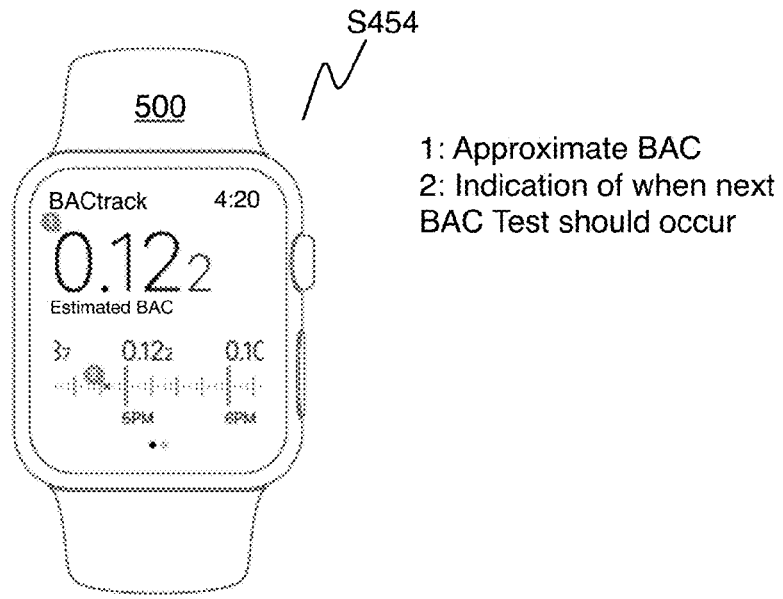
Figure 16E:
Figure 16F:
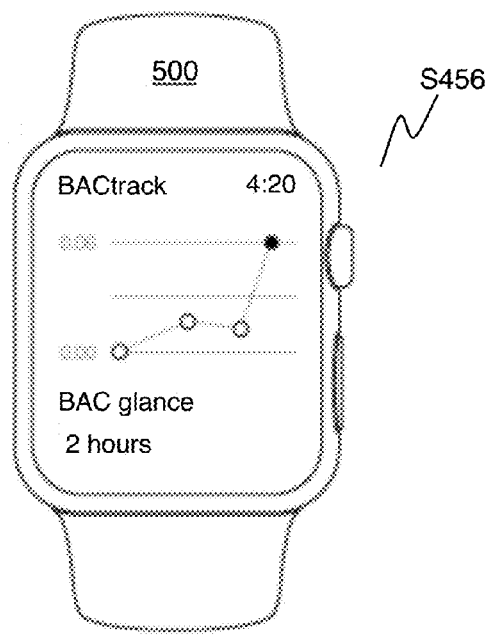
Figure 16G:
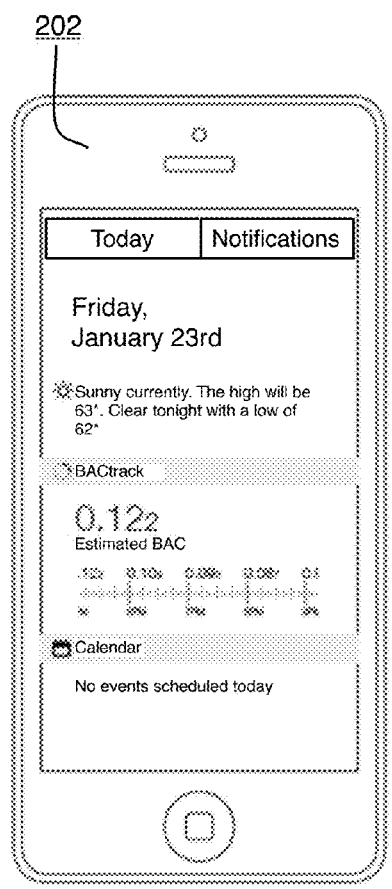

In relation to Block S450, rendering an analysis can be performed according to an embodiment, variation, or example of notification provision described in Block S170 above; however, rendering the analysis can additionally or alternatively be performed in any other suitable manner. In one variation, Block S450 can comprise transmitting commands that prompt the mobile computing device to render an analysis derived from the predicted temporal profile and informative of the estimated time point at the user interface. In specific examples, Block S450 can include one or more of: rendering a countdown timer that actively displays a time duration until the estimated time point at which the user will reach the state of sobriety S451, as shown in FIG. 16A; rendering a summary that displays the current estimation of the value of the intoxication metric for the user and the estimated time point at which the user will reach the state of sobriety S452, as shown in FIG. 16B; rendering a clock that actively displays a set of estimated values of the intoxication metric for the user at each of a set of time points S453 (e.g., past, current, and/or future time points), as shown in FIG. 16C; rendering a clock that displays time points at which the user will be reminded to provide a breath sample S454, as shown in FIG. 16D; rendering a value of the intoxication metric derived from provision of a breath sample at a historical time point, including a location at which the breath sample was provided and a time point at which the breath sample was provided S455, as shown in FIG. 16E; and rendering historical values of the intoxication metric derived from breath samples provided by the user in graphical form S456 (e.g., as a line graph), as shown in FIG. 16F. In Block S450, renderings derived from the analysis are preferably provided to the user at a display of the wearable mobile computing device (e.g., wrist-borne mobile computing device, head-mounted mobile computing device, etc.); however, renderings derived from the analysis can additionally or alternatively be provided to the user at a display of a mobile device in communication with the sample receiving module, an example of which is shown in FIG. 16G.

As shown in FIG. 1A, the method 100 can further comprise Block S180, which recites: generating a longitudinal prediction of an effect of the user's alcohol consumption, based upon the set of signals and the analysis. Block S180 functions to enable a determination of a change in the user's alcohol tolerance level over time, which can be used to inform the user of adverse effects of alcohol consumption or abuse. The longitudinal prediction is preferably based upon accumulated analyses, such as analyses generated in multiple instances of Block S160, but can be formed based upon any other suitable data. In variations, the longitudinal prediction is based upon tracking of the user's intoxication metric values (e.g., from predicted temporal profiles) for given amounts of alcohol consumed over time, in relation to changes in any one or more of: performance of the sobriety task, behavior, impairment, weight gain, weight loss, metabolism, organ damage, organ recovery, and any other suitable expression of intoxication.

Figure 6:
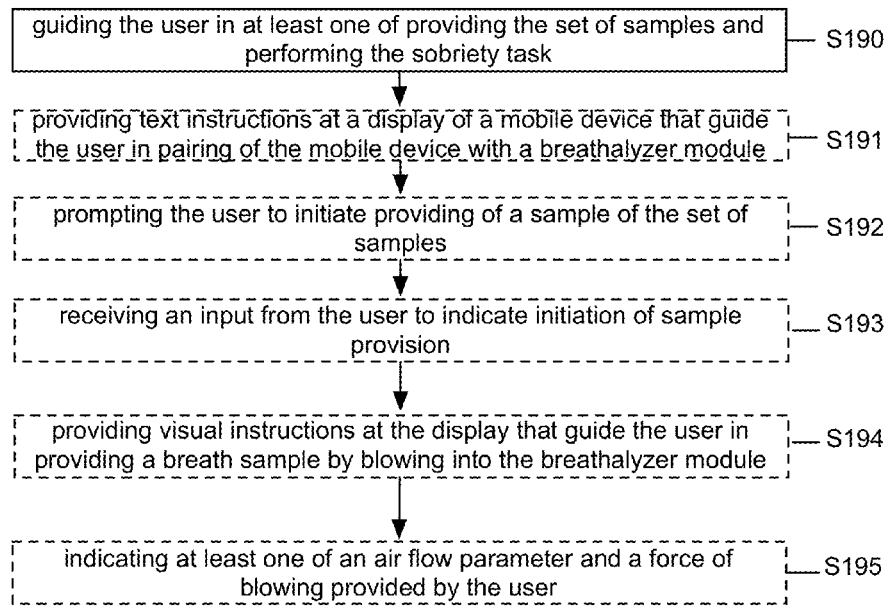
FIG. 6 depicts a schematic of a portion of an embodiment of a method for monitoring intoxication.

As shown in FIGS. 1 and 6, the method 100 can further comprise Block S190, which recites: guiding the user in at least one of providing the set of samples and performing the sobriety task. Block S190 functions to ensure that the user has provided the set of samples properly, and/or to provide the user with instructions in performing the sobriety task. In guiding the user in providing the set of samples, Block 190 is preferably implemented at a sample collection module and/or a user interface of an application executing at an electronic device (e.g., mobile device) of the user; however, guiding the user in providing the set of samples can additionally or alternatively be performed in any other suitable manner. In guiding the user in performing the sobriety task, Block 190 is preferably implemented at a user interface of an application executing at an electronic device (e.g., mobile device) of the user; however, guiding the user in performing the sobriety task can additionally or alternatively be performed in any other suitable manner. In variations of the method 100 including guiding the user in providing the set of samples, Block S190 preferably includes providing instruction to the user in one or more of a visual format, an auditory format, and a haptic format, but can additionally or alternatively include providing instruction to the user in any other suitable format. Furthermore, Block S190 can include pairing of a user interface, at which guidance of the user is provided, with a sample collection module by a wired and/or a wireless link (e.g., Bluetooth, WiFi). In examples, providing instruction can thus be implemented using one or more of a display (e.g., of a mobile device of the user and/or a display of a sample collection module), a speaker unit (e.g., of a mobile device and/or of a sample collection module), a lighting module (e.g., an LED array of a mobile device and/or of a sample collection module), and a vibration motor (e.g., of a mobile device and/or of a sample collection module).

In a specific example of guiding the user in providing the set of samples, Block S190 is implemented at a mobile device coupled with a breathalyzer module. In the specific example, Block S190 includes: providing text instructions at a display of the mobile device that guide the user in pairing of the mobile device with the breathalyzer module S191, and prompting the user to initiate provision of a sample of the set of samples S192. The specific example further includes receiving an input from the user to indicate initiation of sample provision S193 (e.g., by selecting a button, by speaking into the mobile device), which causes the mobile device to send an initiation signal to the breathalyzer module. Block S193 thus facilitates activation of the breathalyzer, which can include any one or more of warming up the breathalyzer, burning off excess alcohol, calibrating the breathalyzer, and any other suitable step. The specific example further includes providing visual instructions at the display that guide the user in providing a breath sample by blowing into the breathalyzer module S194 (e.g., by using a graphical object that indicates the amount of time that the user needs to blow into the breathalyzer). In the specific example, a microphone within the breathalyzer module senses that the user is providing the sample, and transmits a signal to the mobile device to indicate that the user is providing the breath sample. An application executing at the mobile device can then display an indicator (e.g., a countdown indicator) to guide the user in providing the breath sample over an adequate duration of time. If the user provides an inadequate or otherwise unsuitable breath sample, the application can provide an error notification to the user. In variations of the specific example, guiding the user can further include indicating at least one of an air flow parameter and a force of blowing (e.g., using a pressure sensor, using a flow sensor) provided by the user S195 at a display of the mobile device and/or the breathalyzer module, and indicating improper breath sample provision if the air flow parameter and/or the force of blowing does not satisfy a threshold condition S196. The specific example thus provides greater assurance that the user has properly provided a sample of the set of samples.

In variations of the method 100 including guiding the user in performing the sobriety task, Block S190 can include providing instruction to the user in one or more of a visual format, an auditory format, and a haptic format, but can additionally or alternatively include providing instruction to the user in any other suitable format. In examples analogous to those described above, providing instruction can thus be implemented using one or more of a display (e.g., of a mobile device of the user), a speaker unit (e.g., of a mobile device), a lighting module (e.g., an LED array of a mobile device), and a vibration motor (e.g., of a mobile device). The guidance in Block S190 is thus provided in a consistent format that strengthens analyses generated from the user's performance of the sobriety task.

Also shown in FIG. 1A, the method 100 can further comprise Block S210, which recites: transmitting at least one of the predicted temporal profile, the analysis, and the notification to an entity. Block S210 functions to share at least one aspect related to the user's intoxication state with another entity (e.g., caretaker, friend, family member, supervisor) associated with the user, which can facilitate monitoring of the user's intoxication. The transmission preferably shares at least one of the predicted temporal profile, the analysis, and the notification in a secure manner (e.g., over a private message, with a unique URL, etc.), but can alternatively involve sharing in a non-secure manner. In variations, at least one of the predicted temporal profile, the analysis, and the notification can be provided to the entity along with any relevant activity and/or location information, as provided in the supplementary dataset. In examples, the notification can thus allow the entity to locate the user even when the user is unable or unwilling to communicate, and can prepare the entity to accommodate the intoxication state of the user (e.g., by sending a taxicab to pick the user up). In these examples and variations, the notification can also be provided in any suitable manner (e.g., messaging client, by a social network, etc.).

The method 100 can further include any other suitable blocks or steps that facilitate monitoring of a user's intoxication. Additionally, as a person skilled in the field of intoxication monitoring devices will recognize from the previous detailed description and from the figures and claims, modifications and changes can be made to the embodiments, variations, examples, and specific applications of the method 100 described above without departing from the scope of the method 100.

2. System

Figure 7A:
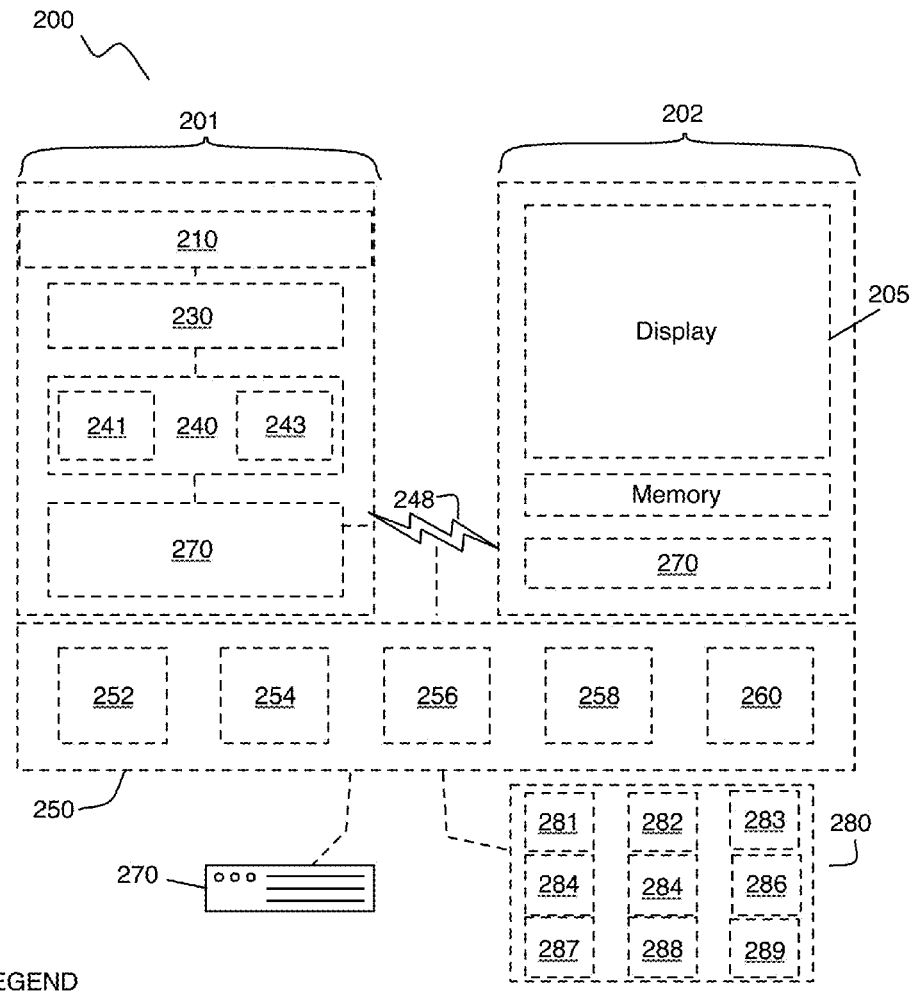
FIGS. 7A-7C depict schematics of embodiments of a system for monitoring intoxication.

As shown in FIG. 7A, an embodiment of a system 200 for monitoring intoxication of a user includes: a sample receiving module 210 configured to accept a set of breath samples of the user at a set of time points; a sample processing module 230 configured to analyze the set of breath samples; an electronics subsystem 240 comprising a power module 241 configured to power the sample processing module 230 and a conditioning module 243 configured to process signals generated by a sensor of the sample processing module 230; a data link 248 coupled to the sample processing module and configured to communicate a set of signals derived from the set of breath samples; and a processing subsystem 250 including a first module 252 configured to receive the set of signals, a supplementary dataset, and a performance dataset characterizing the user's performance of a sobriety task proximal to at least one time point of the set of time points; a second module 254 configured to determine a set of values of an intoxication metric, derived from the set of signals; a third module 256 configured to generate a predicted temporal profile of the intoxication metric for the user based upon the set of values, the set of time points, and the supplementary dataset; a fourth module 258 configured to generate an analysis of the user's sobriety as derived from the performance dataset, and a fifth module 260 configured to generate a notification based upon the predicted temporal profile and the analysis. The system 200 can further include any other suitable element that facilitates monitoring of the user's intoxication, such as a storage module 270 configured to store and/or transmit at least one of the analysis, the notification, and the predicted temporal profile.

The system 200 functions to provide a tool that allows a user to monitor his/her alcohol consumption and behavioral effects of intoxication in a compelling and intuitive manner. The system 200 can also guide a user's behavior at various stages of intoxication, by providing notifications related to the user's intoxication state. In this regard, the system can provide short-term and/or long-term predictions of a state of the user, in quantitative and qualitative manners, such that the user learns about the physiological and/or behavioral effects of his/her alcohol consumption. The system 200 can also incorporate a social component, wherein information related to a user's intoxication-induced behavior and/or physiological state can be communicated to another entity (e.g., a supervisor, a caretaker, a family member, an acquaintance).

2.1 System—Sample Receiving Module

The sample receiving module 210 includes a body 212 defining a cavity 215 configured to accept the set of breath samples of the user at a set of time points, and functions to provide a module that facilitates reception and processing of the set of breath samples.

Figure 7B:
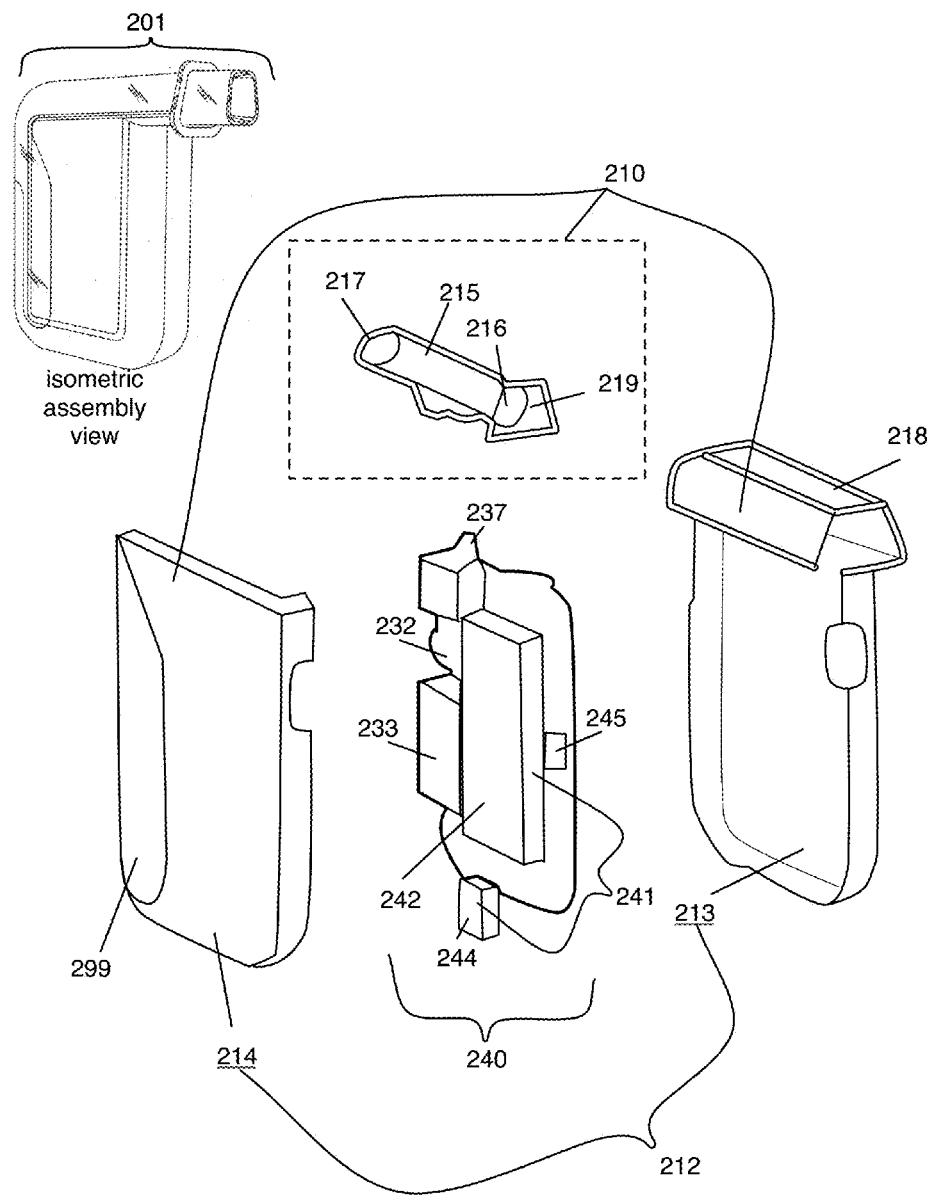
Figure 7C:
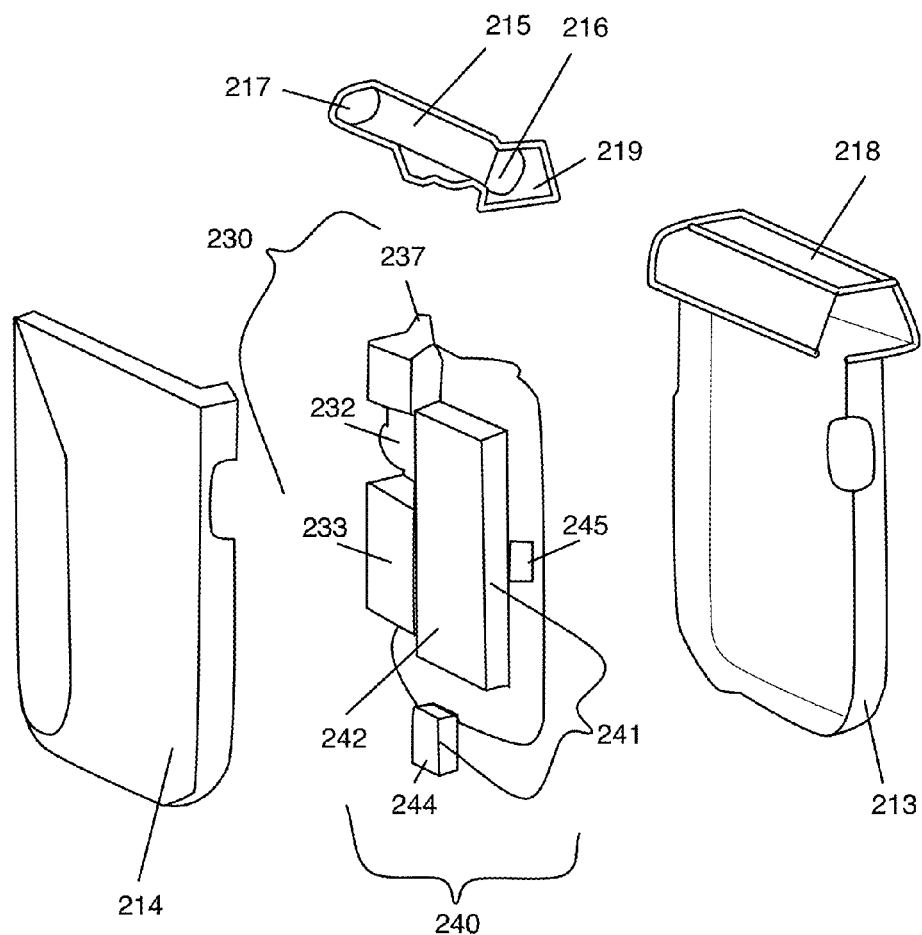

The body 212 is configured to enclose at least a portion of the system 200, and functions to protect elements of the system 200 over the lifetime usage of the system 200. In some embodiments, the body can further function to enhance portability of the system 200, such that the user can conveniently bring the sample receiving module wherever he/she goes. As shown in FIG. 7B, the body 212 can include a first body portion 213 and a second body portion 214 coupled together to form an interior chamber. In some variations, at least one of the first body portion 213 and the second body portion 214 can include a transparent or translucent portion 299 that allows elements within the body 212 to be visible or identifiable. However, in other variations, the first body portion 213 and the second body portion 214 can be substantially opaque to hide elements within the body 212. The body 212 is preferably composed of a polymer (e.g., polystyrene) that is processed to define features of the body (e.g., by machining, by injection molding, by casting, by printing, etc.); however, the body can alternatively be composed of any other suitable material and processed by any other suitable process. In a specific example, as shown in FIG. 7B, the first body portion 213 and the second body portion 214 couple together to form an approximately rectangular prism with rounded corners, wherein the first body portion 213 includes a transparent portion 299 located at the periphery of the first body portion 213 that allows visualization of elements internal to the body 212.

The cavity 215 is preferably included within a portion of the interior chamber of the body 212, is coupled to the sample processing module 230, and comprises a first aperture 216 and a second aperture 217, in communication with the first aperture 216, configured to facilitate sample inflow and outflow. The cavity 215 thus functions to facilitate transmission of a sample from the user to be analyzed by the sample processing module 230. The first aperture 216 and the second aperture 217 can be substantially identical in geometry, such that the cavity has an axis of symmetry (e.g., longitudinal axis of symmetry, transverse axis of symmetry), and such that each of the first aperture 216 and the second aperture 217 can function as both a sample inlet and a sample outlet; however, the first aperture 216 and the second aperture 217 can alternatively be non-identical in geometry or in any other suitable manner, as shown in FIG. 7B, such that the cavity 215 has an orientation that is identifiable by the user and is configured to only receive a sample from one of the first aperture 216 and the second aperture 217. In one variation, the cavity 215 can be defined by a tube form factor, as shown in FIG. 7B; however, the cavity 215 can alternatively be defined by any other suitable form factor that facilitates transmission of the sample from the user. The cavity 215 can be of unitary construction with the body 212, can be physically coextensive with the body 212, or can be coupled to the body 212 (e.g., to an interior portion of the body 212, to an exterior portion of the body 212) in any other suitable manner. Similar to the body 212, the cavity 215 can also include a transparent or translucent portion that can be illuminated (e.g., by a lighting module) to provide an indicator function for the user. In a specific example, as shown in FIG. 7B, the cavity 215 is partially coupled to the body 212 by a housing 218 that couples the cavity 215 to a peripheral portion of the body 212, wherein the housing 218 includes apertures that align with and provide access to the first aperture 216 and the second aperture 217.

In some variations, the sample receiving module 210 can further include a mouthpiece 219 configured to mechanically couple (e.g., with protrusions/depressions, with slots, with keys, with tabs, with threads, by press fit, etc.) to at least one of the first aperture 216 and the second aperture 217, in order to facilitate sample reception from the user. The mouthpiece 219 can be configured to permanently couple to at least one of the first aperture 216 and the second aperture 217, semi-permanently couple to at least one of the apertures 216, 217, or reversibly couple to at least one of the apertures 216, 217. Furthermore, the mouthpiece 219 can define unique identifiers (e.g., colors, textures, geometric features, etc.) that facilitate usage of the system 200 by multiple users. In one specific example, the mouthpiece 219 is configured to be reversibly coupled to the first aperture 216, such that the mouthpiece 219 is a disposable and replaceable element of the sample receiving module 210. In alternative variations of the sample receiving module 210, however, the mouthpiece 219 can be of unitary construction with one of the first aperture 216 and the second aperture 217.

2.2 System—Sample Processing Module

The sample processing module 230 is configured to couple to the cavity 215 of the sample receiving module 210, and functions to facilitate analysis of the set of breath samples and generation of a set of signals from the set of breath samples. As such, the sample processing module 230 preferably includes a sensor 232 coupled to an electronics subsystem 240, wherein the sensor interacts with a sample of the set of breath samples and the electronics subsystem 240 conditions signals produced based upon the sensor-sample interaction for transmission to a processing subsystem for further analysis. The sample processing module 230 is preferably housed within the body 212 of the sample receiving module 210, but can alternatively be configured relative to the sample receiving module 210 in any other suitable manner. The sample processing module 230 can, alternatively, include any other suitable elements that facilitate sample processing and transmission.

The sensor 232 is preferably a fuel cell sensor that enables measurement of a user's BAC by an electrochemical process. In particular, the fuel cell sensor is configured to produce an electrical current in response to oxidation of alcohol carried in a breath sample, wherein the magnitude of the produced electrical current varies in a predictable manner according to the amount (e.g., relative volume) of alcohol carried in the breath sample. As such, in some variations, the sensor 232 can be incorporated into a fuel cell subsystem including a pump 233 configured to drive a breath sample received from at least one of the first aperture 216 and the second aperture 217, through an intake 237 toward the sensor 232.

The sensor 232 can alternatively be a semiconductor sensor that produces a change in electrical resistance in response to an alcohol-dioxide reaction, wherein the magnitude of the change in resistance varies in a predictable manner according to the amount (e.g., relative volume) of alcohol carried in the breath sample. In a specific example, the semiconductor sensor can incorporate tin-oxide as a sensing element; however, variations of the semiconductor sensor can alternatively use any other suitable sensing element. In other variations of the sensor 232, the sensor can include a spectrophotometer configured to produce a signal in response to absorbed or emitted light from alcohol molecules carried in the breath sample, or any other suitable type of sensor.

The electronics subsystem 240 comprises a power module 241 configured to power the sample processing module 230 and a conditioning module 243 configured to process signals generated by the sensor 232 for transmission and further analysis. As such, the electronics subsystem 240 functions to provide power to elements of the system 200, condition and/or preprocess signals generated from received breath samples, and facilitate transmission of signals to a processing subsystem for further analysis. The electronics system 240 preferably incorporates or is configured to couple to a data link 248 for transmission of signals from the sample processing module 230 to a processing subsystem for further processing and analysis. Preferably, the electronics subsystem 240 complies with relevant technical and safety standards, such that the system 200 is configured for "home-use"; however, the electronics subsystem can be configured in any suitable manner.

The power module 241 of the electronics subsystem 240 functions to provide regulated and unregulated electrical power to the sample processing module 230 and to allow power storage for the sample processing module 230. The power module 241 preferably comprises a battery 242, such as a lithium-ion battery that is configured to be rechargeable, but can alternatively comprise any other suitable rechargeable battery (e.g., nickel-cadmium, metal halide, nickel metal hydride, or lithium-ion polymer). Alternatively, the power module 241 can comprise a non-rechargeable battery (e.g., alkaline battery) that can be replaced to further enhance modularity in the system 200. The power module 241 can be configured to have any appropriate profile such that the power module 241 provides adequate power characteristics (e.g., cycle life, charging time, discharge time, etc.) for the sample processing module 230 within physical constraints provided by the body 212 of the sample receiving module 210.

In variations where the battery 242 of the power module 241 is rechargeable, the electronics subsystem 240 can also comprise a coil of wire and associated electronics that function to allow inductive charging of the battery by an external power source and the power module 241. Inductive charging provided by the charging coil thus also facilitates patient mobility while interacting with the system 200, such that the patient can be extremely mobile while monitoring his/her intoxication. In alternative variations, however, the charging coil can be altogether omitted (e.g., in variations without a rechargeable battery), or replaced or supplemented by a connection 244 (e.g., USB connection) configured to provide wired charging of a rechargeable battery.

The conditioning module 243 functions to preprocess signals generated by the sensor 232 prior to transmission from the sample processing module 230, and can additionally function to regulate elements of the electronics subsystem 240. The conditioning module preferably comprises signal conditioning elements, including one or more of: an analog-to-digital converter (e.g., to convert analog signals sensor 232), an amplifier, and a filter for processing signals prior to transmission. In some variations, the conditioning module 243 can include a microprocessing subsystem configured to direct signal conditioning functionalities of the conditioning module 243 and a voltage regulator configured to protect elements of the electronics subsystem 240 from overvoltage and/or under-voltage states.

The electronics subsystem 240 can additionally or alternatively comprise any other suitable element that facilitates intoxication monitoring. Furthermore the electronics subsystem 240 can be coupled to a user control module 245 that interfaces with the electronics subsystem 240, such that manual control of any aspect of the sample receiving module 210 and/or the sample processing module 230 can be performed by the user or any other suitable entity. The user control module 245 can comprise a power toggle (e.g., on/off button) for activating and/or deactivating the sample receiving module 210. The user control module 245 can further include input devices that allow the user to indicate initiation of sample provision. Preferably, the user control module 245 provides a minimal number of controls (e.g., an on/off button, a sample provision initiation button), but can provide any suitable number of manual controls. The user control module 245 can be touch-activated (e.g., with a touch screen, buttons, dials, knobs, sliders), or can be activated using any other suitable manner (e.g., sound activation). Preferably, the user control module 245 is integrated with the electronics subsystem 240, but in other alternative variations, the user control module 245 can be implemented remotely from the system sample processing module 230, for example, using an application executing on a mobile device of the patient.

The data link 248 functions to transmit an output of at least one element of the electronics subsystem 240 to one or more of: a mobile computing device 202, a processing subsystem 250, and any other suitable computing device (e.g., desktop computer, laptop computer, tablet, smartphone, wrist-borne mobile computing device, head-mounted mobile computing device, health tracking device, server, cloud, etc.). Preferably, the data link 248 is a wireless interface; however, the data link 248 may alternatively be a wired connection. In a first variation, the data link 248 can include a Bluetooth module that interfaces with a second Bluetooth module included in the mobile device or external element, wherein data or signals are transmitted by the data link 248 to/from the mobile device or external element over Bluetooth communications. The data link of the first variation can alternatively implement other types of wireless communications, such as 3G, 4G, radio, or Wi-Fi communication. In the first variation, data and/or signals are preferably encrypted before being transmitted by the data link 248. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In a second variation, the data link 248 is a wired connection such that the electronics subsystem 240 can communicate with the mobile device and/or any external computing element through a jack of the mobile device and/or external computing element. In one specific example of the data link 248 that includes a wired jack, the data link 248 is configured only to transmit output signals from the electronics subsystem 240. In another specific example, the data link 248 is configured to transmit data to and from at least one element of the electronics subsystem 240 and a mobile device (e.g., for pairing of the mobile device and the electronics subsystem, for synchronization between the mobile device and the electronics subsystem). In this example, the data link 248 can transmit output signals into the mobile device through the microphone input of the audio jack of the mobile device and can retrieve data from the audio output of the audio jack of the mobile device. In variations of this example, the data link 248 can additionally or alternatively communicate with the mobile device via inter-integrated circuit communication (I2C), one-wire, master-slave, or any other suitable communication protocol. However, the data link 248 can transmit data in any other way and can include any other type of wired connection (such as a USB wired connection) that supports data transfer between the electronics subsystem 240, the mobile device, and/or any other suitable computing element.

2.3 System—Processing Subsystem

The processing subsystem 250 includes a first module 252 configured to receive the set of signals from the sample processing module 230, a supplementary dataset characterizing at least one of a demographic profile of the user and a physiological state of the user, and a performance dataset characterizing the user's performance of a sobriety task proximal to at least one time point of the set of time points. The processing subsystem preferably also includes a second module 254 configured to determine a set of values of an intoxication metric, derived from the set of signals; a third module 256 configured to generate a predicted temporal profile of the intoxication metric for the user based upon the set of values, the set of time points, and the supplementary dataset; a fourth module 258 configured to generate an analysis of the user's sobriety as derived from the performance dataset, and a fifth module 260 configured to generate a notification and/or transmit commands to a mobile computing device to render information based upon the predicted temporal profile and the analysis. As such, the processing subsystem preferably functions to implement at least a portion of the method 100 described in Section 1 above, but can alternatively be configured to perform any other suitable method that facilitates monitoring of the user's intoxication. The first module 252, the second module 254, the third module 256, the fourth module 258, and the fifth module 260 can be implemented at a single processing unit, or can be implemented using multiple processing units (e.g., implemented in one or more of: the sample receiving module, the sample processing module, the mobile computing device, a cloud platform, a remote server, a computer machine, etc.).

2.4 System—Other Elements

The system 200 can additionally further comprise a storage module 270, which functions to retain data generated during use of the system 200. The storage module 270 can be implemented with any one or more of: the electronics subsystem 240, mobile device, personal computer, web browser, external server (e.g., cloud), local server, and any combination of the above, in a network configured to transmit, store, and receive data. Preferably, data from the storage module 270 is automatically transmitted to any appropriate external device continuously; however, data from the storage module 270 can alternatively be transmitted intermittently (e.g., every minute, hourly, daily, or weekly). In one example, data generated by any element can be stored on a portion of the storage module 270 when the data link 248 is not coupled to an element external to the electronics subsystem 240. However, in the example, when a link is established between the data link 248 and an external element, data may then be automatically transmitted from the storage module 270. In other examples, the storage module 270 can alternatively be manually prompted to transmit stored data by a user or other entity.

As shown in FIG. 7A, the system 200 can additionally include a supplementary sensing module 280 configured to communicate with the processing subsystem 250, wherein the supplementary sensing module functions to facilitate reception and/or generation of data related to any one or more of: food consumption (e.g., amount/rate of consumption), beverage consumption (e.g., amount/rate of consumption), medication usage, activity (e.g., exercise, rest, sleep), biometric information (e.g., heart rate, respiration rate, pupilometric information, neural activity information, etc.), emotional state (e.g., stress state), user location information, and another other suitable type of supplementary information (e.g., environmental data). As such, the supplementary sensing module 280 can include any one or more of: an image sensor 281 (e.g., for generation of image data related to food, drink, or medication usage), an accelerometer 282 (e.g., for activity data), a gyroscope 283 (e.g., for activity data), a location sensor 284 (e.g., GPS), and a biometric sensor 285 (e.g., heart rate monitor, respiration sensor, blood pressure sensor, electroencephalogram activity sensor, etc.). The supplementary sensing module can also include a manual input module 286 configured to receive manual inputs from the user or another entity that provides supplementary data. In some variations, involving automated generation of a supplementary dataset as described in Section 1 above, the supplementary sensing module 280 can include an aggregation module 287 configured to access, retrieve, and/or aggregate content (e.g., digital content) from different sources (e.g., social network accounts, search results, etc.), and can additionally include object recognition and/or text recognition modules 288, 289, respectively to enable automatic identification of items that the user consumes. The supplementary sensing module can additionally comprise a tagging module configured to tag supplementary data with time information to facilitate analysis and processing of data by the processing subsystem 250.

Figure 8:
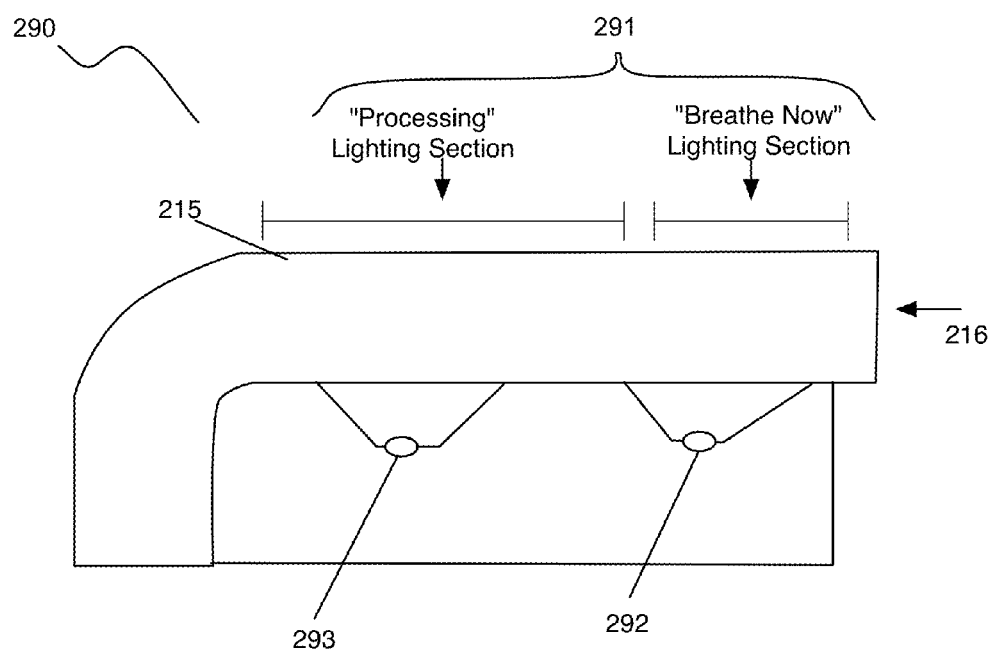
FIG. 8 depicts an example of a portion of a system for monitoring intoxication.

As shown in FIG. 8, the system 200 can additionally include an indicator module 290, which functions to guide the user in properly providing a sample of the set of samples. The indicator module 290 can be implemented using an application executing at a mobile device of the user, and in variations, can incorporate functions of one or more of: a display of the mobile device, an LED of the mobile device, a speaker of the mobile device, a vibration motor of the mobile device, and any other suitable element of the mobile device. The indicator module 290 can additionally or alternatively be implemented using a lighting module 291 configured to couple to the sample receiving module 210 and the sample processing module 230. One variation of the lighting module 291 includes a set of light emitting diodes (LEDs) configured to indicate that the user should initiate provision of a breath sample, that the sample processing module 230 is processing the breath sample, and/or that the user has improperly provided a breath sample. In a specific example, as shown in FIG. 8, the lighting module 291 includes a first LED 292 and a second LED 293 oriented proximal to the cavity 215 (e.g., a tube configured to receive the breath sample), such that the first LED 292 and the second LED 293 illuminate the cavity to provide an indicator function for the user. In the specific example, the first LED 292 functions as a visual cue that guides the user in submitting a breath sample into the cavity 215, and the second LED 293 functions as a visual cue that indicates that the sample processing module 230 is currently processing the breath sample provided by the user. As such, the first LED 292 and the second LED 293 in the specific example are both coupled to the electronics subsystem 240 of the sample processing module 230. Other variations of the indicator module 290 can include any other suitable indication elements in communication with any other suitable element of the system 200.

Variations of the method 100 and system 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processing subsystem. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processing subsystem, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for informing a user of an intoxication state over time, comprising:
   at a sample receiving module coupled to a wrist-borne device, receiving a set of samples from a body region of the user within a time window;
   at a processing subsystem in communication with the wrist-borne device, generating a sample signal derived from an interaction between the set of samples and a fuel cell sensor in communication with the sample receiving module;
   at the processing subsystem, determining a predicted temporal profile of an alcohol content metric from the sample signal, the predicted temporal profile including a predicted value of the alcohol content metric at a time point outside of the time window; and
   transmitting a set of commands, from the processing subsystem to a user interface device coupled to at least one of the processing subsystem, the sample receiving module, and the wrist-borne device, that prompt the user interface device to provide an output derived from the predicted temporal profile to the user.

2. The method of claim 1, wherein receiving the set of samples comprises receiving a set of alcohol-containing samples from the body region of the user within the time window.

3. The method of claim 1, wherein determining the predicted temporal profile of the alcohol content metric comprises transforming the sample signal into a blood alcohol content temporal profile.

4. The method of claim 1, further comprising: receiving an additional sample at the sample receiving module at a second time point outside of the time window, and adjusting the predicted temporal profile based upon the additional sample and the second time point.

5. The method of claim 1, further comprising: prompting the user to provide the sample at the wrist-borne device.

6. The method of claim 1, wherein the user interface device comprises a display, wherein transmitting the set of commands comprises prompting the display to render a countdown timer that actively displays a time duration until an estimated time point at which the user will reach a state of sobriety.

7. The method of claim 1, further comprising: extracting a user activity dataset from user activity monitoring devices associated with the user, generating a set of associations between events of the user activity dataset and the predicted temporal profile, and, at the user interface device, providing insights derived from the set of associations to the user.

8. The method of claim 1, further comprising: through a set of notifications provided at the user interface device, guiding behavior of the user at various stages of intoxication, based upon the predicted temporal profile of the alcohol content metric.

9. The method of claim 1, wherein transmitting the set of commands comprises providing the user with a notification dissuading performance of an activity even though the user is below a legal limit of intoxication.

10. The method of claim 1, further comprising: at the user interface device, prompting the user to provide an input indicative of an estimated intoxication state of the user, generating a comparison between the estimated intoxication state of the user and an actual intoxication state of the user captured in the sample signal, and rendering the output at the user interface device, the output informing the user of a difference between the estimated intoxication state and the actual intoxication state.

11. A method for informing a user of an intoxication state over time, comprising:
- at a sample receiving module coupled to a wrist-borne device, receiving a set of samples from a body region of the user;
- at a processing subsystem in communication with the wrist-borne device, generating a sample signal derived from an interaction between the set of samples and a fuel cell sensor in communication with the sample receiving module;
- at the processing subsystem, determining a temporal profile of an alcohol content metric from the sample signal; and
- from the processing subsystem, prompting a user interface device associated with the user to provide a notification derived from the temporal profile to the user.

12. The method of claim 11, wherein determining the temporal profile of the alcohol content metric comprises transforming the sample signal into a profile of blood alcohol content over a time window.

13. The method of claim 12, wherein the set of samples comprises non-breath material from the body region of the user.

14. The method of claim 11, wherein prompting the user to provide the set of samples comprises guiding the user in provision of the set of samples by rendering instructions at a display of the user interface device.

15. The method of claim 11, further comprising: providing a set of tasks at a mobile device in communication with the sample receiving module, wherein the set of tasks includes a coordination testing task.

16. The method of claim 15, wherein providing the set of tasks includes detecting performance of a task of the set of tasks by the user with at least one of: an image sensor, a touch display, and an accelerometer of the mobile device.

17. The method of claim 11, further comprising: through a set of notifications provided at the user interface device, guiding behavior of the user at various stages of intoxication, based upon the temporal profile of the alcohol content metric.

18. A system for monitoring intoxication of a user, comprising:
- a sensor body operable to accept a set of samples from a body region of the user within a time window;
- a sample processing module in communication with the sensor body and a mobile computing device of the user, and operable to transform the set of samples into a sample signal;
- a data link coupled to the sample processing module and operable to transmit the sample signal; and
- a processor operable between:
  - a first mode that receives the sample signal,
  - a second mode that transforms the sample signal into a set of values of an alcohol content metric,
  - a third mode that generates a temporal profile of the alcohol content metric from the set of values and supplementary information from the user, and
  - a fourth mode that provides an output derived from the temporal profile to a user interface of the mobile computing device of the user.

19. The system of claim 18, further comprising a wrist-borne device, the wrist-borne device in communication with the sample processing module and the data link.

20. The system of claim 18, wherein the sensor body comprises a fuel cell sensor operable to produce an electrical current in response to oxidation of alcohol carried in the set of samples.

21. The system of claim 18, wherein the set of samples is a set of alcohol containing samples from the body region of the user.

* * * * *